US011512317B2

(12) United States Patent
Kim et al.

(10) Patent No.: US 11,512,317 B2
(45) Date of Patent: Nov. 29, 2022

(54) RECOMBINANT BCG EXPRESSING HIV-1 P24 USING PMYONG2 VECTOR SYSTEM AND USE THEREOF

(71) Applicant: SEOUL NATIONAL UNIVERSITY R & DB FOUNDATION, Seoul (KR)

(72) Inventors: Bum-Joon Kim, Seoul (KR); Byoung-Jun Kim, Uiwang-Si (KR); Bo-Ram Kim, Seoul (KR)

(73) Assignee: SEOUL NATIONAL UNIVERSITY R & DB FOUNDATION, Seoul (KR)

( * ) Notice: Subject to any disclaimer, the term of this patent is extended or adjusted under 35 U.S.C. 154(b) by 74 days.

(21) Appl. No.: 17/055,394

(22) PCT Filed: Mar. 27, 2019

(86) PCT No.: PCT/KR2019/003597
§ 371 (c)(1),
(2) Date: Nov. 13, 2020

(87) PCT Pub. No.: WO2019/221383
PCT Pub. Date: Nov. 21, 2019

(65) Prior Publication Data
US 2021/0222179 A1    Jul. 22, 2021

(30) Foreign Application Priority Data

May 14, 2018 (KR) .......... 10-2018-0055059
Mar. 26, 2019 (KR) .......... 10-2019-0034183

(51) Int. Cl.
| | |
|---|---|
| C12N 15/74 | (2006.01) |
| A61P 31/18 | (2006.01) |
| A61P 31/06 | (2006.01) |
| A61K 39/04 | (2006.01) |
| A61K 39/21 | (2006.01) |
| C07K 14/005 | (2006.01) |
| C12N 7/00 | (2006.01) |
| A61K 39/00 | (2006.01) |

(52) U.S. Cl.
CPC .......... *C12N 15/74* (2013.01); *A61K 39/04* (2013.01); *A61K 39/21* (2013.01); *A61P 31/06* (2018.01); *A61P 31/18* (2018.01); *C07K 14/005* (2013.01); *C12N 7/00* (2013.01); *A61K 2039/523* (2013.01); *A61K 2039/70* (2013.01); *C12N 2740/16022* (2013.01); *C12N 2740/16034* (2013.01); *C12N 2740/16071* (2013.01)

(58) Field of Classification Search
CPC .......... C12N 15/74; C12N 2740/16234; A61K 39/04
See application file for complete search history.

(56) References Cited

U.S. PATENT DOCUMENTS 5,576,421 A * 11/1996 Saito .................... C07K 14/005
                                                    435/7.1
5,591,632 A    1/1997 O'Donnell et al.

FOREIGN PATENT DOCUMENTS

| KR | 10-1291668 B1 | 8/2013 |
| WO | 2006/076343 A1 | 7/2006 |

OTHER PUBLICATIONS

Kim, B.-J., et al., Mar. 2018, Development of a live recombinant BCG expressing human immunodeficiency virus type 1 (HIV-1) Gag using a pMyong2 vector system: Postential use as a novel HIV-1 vaccine, Front. Immunol. 9:article 643, pp. 1-13.*
Kim, B.-J., et al., Mar. 2017, Recombinant *Mycobacterium smegmatis* with a pMyong2 vector expressing human immunodeficiency virus type 1 Gag can induce enhanced virus-specific immune respones, Sci. Reports 7:4476, pp. 1-11.*
GenBank Submission AIW80596.1, accession No. KM390026.1, submitted Aug. 25, 2014, pp. 1-2.*
Honda, M., et al., Nov. 1995, Protective immune responses induced by secretion of a chimeric soluble protein from recombinant *Mycobacterium bovis* bacillus Calmette-Guerin vector candidate vaccine for human immunodeficiency virus type 1 in small animals, Proc. Natl. Acad. Sci. USA 92:10693-10697.*
Sheets, R. L., et al., 2016, Scientific and regulatory challenges in evaluating clinical trial protocols for HIV-1/AIDS vaccines—a review from a regulatory perspective, Biologicals 44:90-110.*
Rios, A., 2018, Fundamental challenges to the development of a preventive HIV vaccine, Curr. Opin. Virol. 29:26-32.*

(Continued)

*Primary Examiner* — Jeffrey S Parkin
(74) *Attorney, Agent, or Firm* — Vorys, Sater, Seymour and Pease LLP; Mih Suhn Koh

(57) ABSTRACT

Provided is a recombinant BCG employing a pMyong2 vector system to express HIV-1 p24 and a use thereof as a HIV-1 vaccine. rBCG-pMyong2-p24, which is a pMyong2 vector system, was found to induce the upregulation of HIV-1 p24 gag expression in rBCG and infected antigen-presenting cells (APC) and to induce improved p24-specific immune responses in vaccinated mice, compared to rBCG-pAL-p24 in a pAL5000 derived vector system. rBCG-pMyong2-p24 was identified to exhibit a higher p24-specific Ab production level than rSmeg-pMyong2-p24 in the same pMyong2 vector system. Therefore, the recombinant BCG employing rBCG-pMyong2-p24 to express HIV-1 p24 according to the present invention is identified to elicit enhanced immune responses to HIV-1 infection in mouse model systems and thus can be expected to be used as a prime vaccine in the heterologous prime-boost vaccination strategy against HIV-1 infection.

Figure 1:
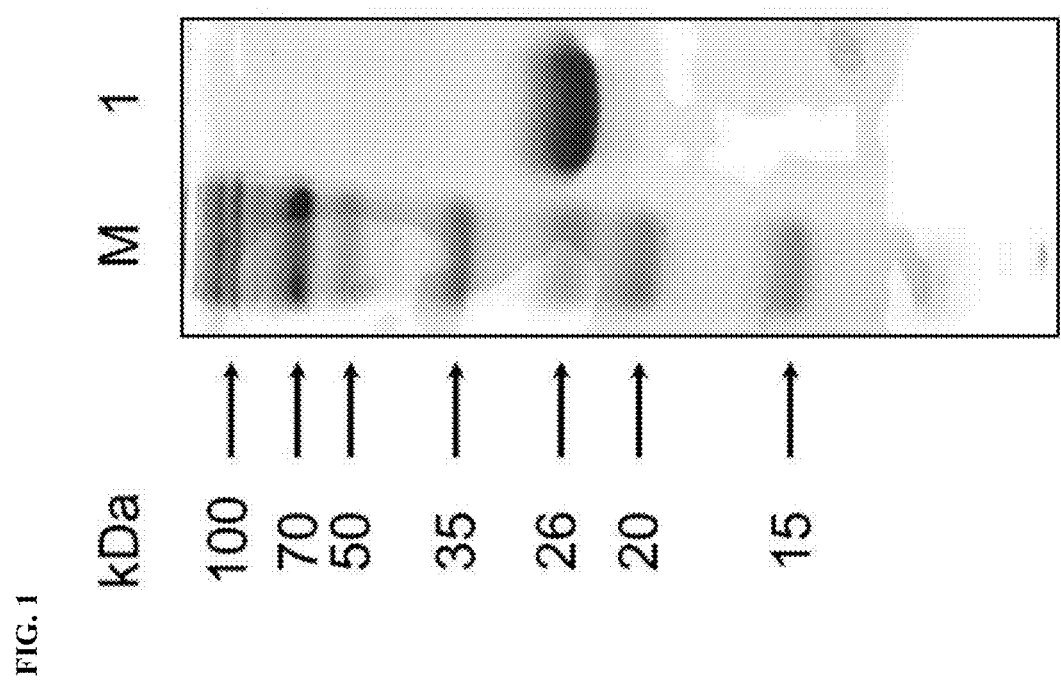

9 Claims, 25 Drawing Sheets
Specification includes a Sequence Listing.

(56) References Cited

OTHER PUBLICATIONS

GenBank: ASV46276.1, "gag protein, partial [Human immunodeficiency virus 1]" (Aug. 25, 2017).
Lee et al., "The development of a novel *Mycobacterium-Escherichia coli* shuttle vector system using pMyong2, a linear plasmid from *Mycobacterium yongonense* DSM 45126T", PLoS One, Mar. 30, 2015, vol. 10(3), e0122897, pp. 1-21.
Kim et al., "Recombinant *Mycobacterium smegmatis* with a pMyong2 vector expressing Human Immunodeficiency Virus Type I Gag can induce enhanced virus-specific immune responses", Scientific reports, Mar. 16, 2017, vol. 7 (44776), pp. 1-11.
Kim et al., "Development of a Live Recombinant BCG Expressing Human Immunodeficiency Virus Type 1 (HIV-1) Gag Using a pMyong2 Vector System: Potential Use as a Novel HIV-1 Vaccine", Frontiers in Immunology, Mar. 27, 2018, vol. 9(643), pp. 1-13.

Office Action dated Jan. 25, 2022 for the corresponding Japanese Patent Application No. 2020-564211.

Aldovini et al., "Humoral and cell-mediated immune responses to live recombinant BCG-HIV vaccines", Nature, 1991, vol. 351, pp. 479-482.

Kim et al., "Recombinant *Mycobacterium smegmatis* with a pMyong2 vector expressing Human Immunodeficiency Virus Type I Gag can induce enhanced virus-specific immune responses", Scientific Reports, 2017, vol. 7, 44776, 11 pages.

* cited by examiner

RECOMBINANT BCG EXPRESSING HIV-1 P24 USING PMYONG2 VECTOR SYSTEM AND USE THEREOF

CROSS-REFERENCE TO RELATED APPLICATIONS

This application claims priority to and the benefit of Korean Patent Application No. 10-2018-0055059, filed on May 14, 2018, Korean Patent Application No. 10-2019-0034183, filed on Mar. 26, 2019 and International Patent Application No. PCT/KR2019/003597, filed on Mar. 27, 2019, the disclosure of which is incorporated herein by reference in its entirety.

SEQUENCE LISTING

The Sequence Listing submitted in text format (.txt) filed on Nov. 13, 2020, named "SequenceListing.txt", created on Nov. 12, 2020 (31.1 KB), is incorporated herein by reference.

TECHNICAL FIELD

The present invention relates to a novel recombinant BCG used for prevention and/or treatment of human immunodeficiency virus type-I (HIV-1) infection, a vaccine composition including the same, a method for preparing the same, and the like. More specifically, the present invention relates to a recombinant BCG live vaccine platform using a novel mycobacterium-Escherichia-coli shuttle vector system (hereinafter, pMyong2, Korean Patent No.: 1012916680000, U.S. Pat. No. 8,841,432).

BACKGROUND ART

Although an HIV-1 infection rate tends to be gradually declining worldwide, an efficient preventive vaccine against HIV-1 still remains an urgent need. Recombinant *Mycobacterium bovis* BCG (rBCG) is a promising strain for HIV-1 vaccine development. Thus, the present invention discloses the potential of rBCG (rBCG-pMyong2-p24) expressing the HIV-1 p24 antigen Gag using a pMyong2 vector in the vaccine application against HIV-1 infection.

Despite the contribution of highly activated antiretroviral therapy (HAART) to control HIV replication in HIV-infected individuals, drug-resistant viruses which are generated after long-term treatment, the costs of expensive drugs, and the like remain as one of several problems to be solved. Therefore, even though the rate of new HIV-1 infections is gradually declining worldwide, there is still a need for efficient preventive vaccines to suppress the further spread of the virus. HIV-specific cellular immunity is primarily induced by HIV-specific T cells having poly-functionality and the ability to proliferate against immunodominant viral peptides, and an efficient immune response to HIV-1 may occur due to these characteristics, so that this cellular immunity, particularly virus-specific cytotoxic T lymphocytes (CTLs) should be a more important component of a host immune system to fight HIV-1.

Based on these facts, various strategies are under development to elicit potent HIV-1-specific CTL and type 1 helper T cell (Th1) responses, including the use of live viral vectors and plasmid DNA vaccines. However, several problems are associated with each of these approaches, including safety issues, so that the actual and practical use thereof is limited. Currently, *Mycobacterium bovis* BCG (BCG), which is currently the most widely administered vaccine worldwide, has been used for 80 years or more as the only live attenuated vaccine to fight tuberculosis (TB). Since BCG can prevent disseminated disease in children, it has been used as a part of the World Health Organization Expanded Program on Immunization (EPI) for childhood vaccination since the early 1970s.

The recombinant form of BCG, i.e., recombinant *Mycobacterium bovis* BCG (rBCG), which has been successfully used to express foreign antigens and induce immune responses, has been considered a vaccine candidate against various infectious agents, including *Borrelia burgdorferi*, *Streptococcus pneumoniae*, *Bordetella pertussis*, rodent malaria, *Leishmania*, measles virus, human immunodeficiency virus type 1 (HIV-1), and simian immunodeficiency virus (SIV). The most practical advantage of the rBCG vector is its high safety. In addition, rBCG demonstrates excellent adjuvant properties, induces long-lasting cellular immune responses that are maintained for at least 1 to 2 years, has a low production cost, is easy to administer, and usually requires only one or two immunizations. Therefore, the above-mentioned advantages of the rBCG-based vaccine over other recombinant vaccine approaches suggest that rBCG could be a potent vaccine against HIV-1 infection, capable of inducing safe, virus-specific immune responses.

DISCLOSURE

Technical Problem

An object of the present invention is to provide recombinant *Mycobacterium bovis* BCG (rBCG) expressing a HIV-1-derived p24 protein and the use thereof as an HIV-1 vaccine.

Despite the promise of a rBCG vector as a potential HIV-1 vaccine, its practical applications as an HIV-1 vaccine is limited because of the low immunogenicity due to the lack of stability and quantity in the heterologous expression of foreign genes within rBCG. Therefore, to obtain sufficient immunogenicity and elicit protective vaccine efficacy, a rBCG dose approximately 10- to 100-fold higher that needed for a practical BCG vaccination against TB in humans are needed. However, the in vivo administration of high doses of BCG may increase the risk of disseminated BCG in immuno-compromised vaccine recipients or act as a driving force for the replication and spread of HIV-1 by hyperactivating T cells.

For this reason, low-dose immunization of rBCG has been recommended for prophylactic vaccination against HIV-1 in order to secure safety, and therefore, the inventors of the present invention aimed to develop a rBCG vaccine for protection from HIV-1, which can exhibit efficacy even at the lower dose required for human vaccination.

Further, the inventors of the present invention aimed to develop a method for treating or preventing AIDS and/or tuberculosis by administering, to an individual, a vaccine composition including a pharmaceutically effective amount of the recombinant *Mycobacterium bovis* BCG as active ingredient, a use of the recombinant *Mycobacterium bovis* BCG for preparing the vaccine, or a use of the recombinant *Mycobacterium bovis* BCG for treating or preventing AIDS and/or tuberculosis.

However, the technical problems which the present invention intends to solve are not limited to the technical problems which have been mentioned above, and other technical problems which have not been mentioned will be apparently understood by a person with ordinary skill in the art to which the present invention pertains from the following description.

Technical Solution

To solve the above-described problems, the present inventors introduced a novel *mycobacterium-E. coli* shuttle vector system using a mycobacterial replicon of pMyong2 which is a linear plasmid capable of inducing increased heterologous gene expression in recombinant *Mycobacterium smegmatis* (rSmeg) and rBCG compared to that using a pAL5000 vector system in the related art, derived from *Mycobacterium* fortuitum through a DSM45126$^T$ genomic analysis of *Mycobacterium yongonense*, a human pathogen member of a *M. avium* complex (MAC).

Furthermore, the present specification showed that rSmeg expressing HIV-1 p24 Gag using a pMyong2 vector system induced enhanced immune responses against HIV-1 p24 Gag in mice, compared to rSmeg in the pAL5000 vector system or using an integrative plasmid, pMV306 system, suggesting the feasibility of the pMyong2 vector system in rSmeg vaccine application.

HIV-1 Gag-specific CD8+ T cell responses may be crucial for immunoregulation of HIV infection. Therefore, in the present invention, HIV-1 Gag p24 was selected as a target antigen for expression in a pMyong2 vector system. Therefore, in the present invention, the pMyong2 vector system was adopted to improve the expression of a foreign HIV-1 p24 Gag gene in rBCG (rBCG-pMyong2-p24). The efficacy of the pMyong2 vector system, that is, its improved recombinant protein production, has been demonstrated in rBCG and rBCG-infected primary bone marrow-derived dendritic cells (hereinafter, referred to as "BMDCs"). In addition, to demonstrate vaccine efficacy, the present inventors explored cellular and humoral immune responses to an HIV Gag protein in vaccinated mice.

The best strategy to improve the potential of rBCG as an HIV vaccine is to use rBCG as a prime vaccine in the prime-boost vaccination protocol and use a safe recombinant viral vector as a booster vaccine, which induces long-lasting efficient virus-specific cellular immunity after vaccination in animal models. In this context, a Th1 response induced by the rBCG vector may contribute to inducing the Gag-specific CTL response. However, the major barrier to the practical use of rBCG as an HIV-1 vaccine is the failure to induce sufficient virus-specific CTL responses to fight viral infection due to the low expression of the foreign HIV-1 antigens in rBCG.

To overcome this limitation, using several strategies including the use of a hemolysin-expressing BCG strain capable of inducing a greater CTL response via the preferential cytoplasmic location of rBCG and a codon optimization for the HIV-1 gag p24 gene in the rBCG system, in the present invention, a pMyong2 shuttle vector system was applied to enhance the expression of the HIV-1 gag p24 gene in the rBCG.

Figure 5B:
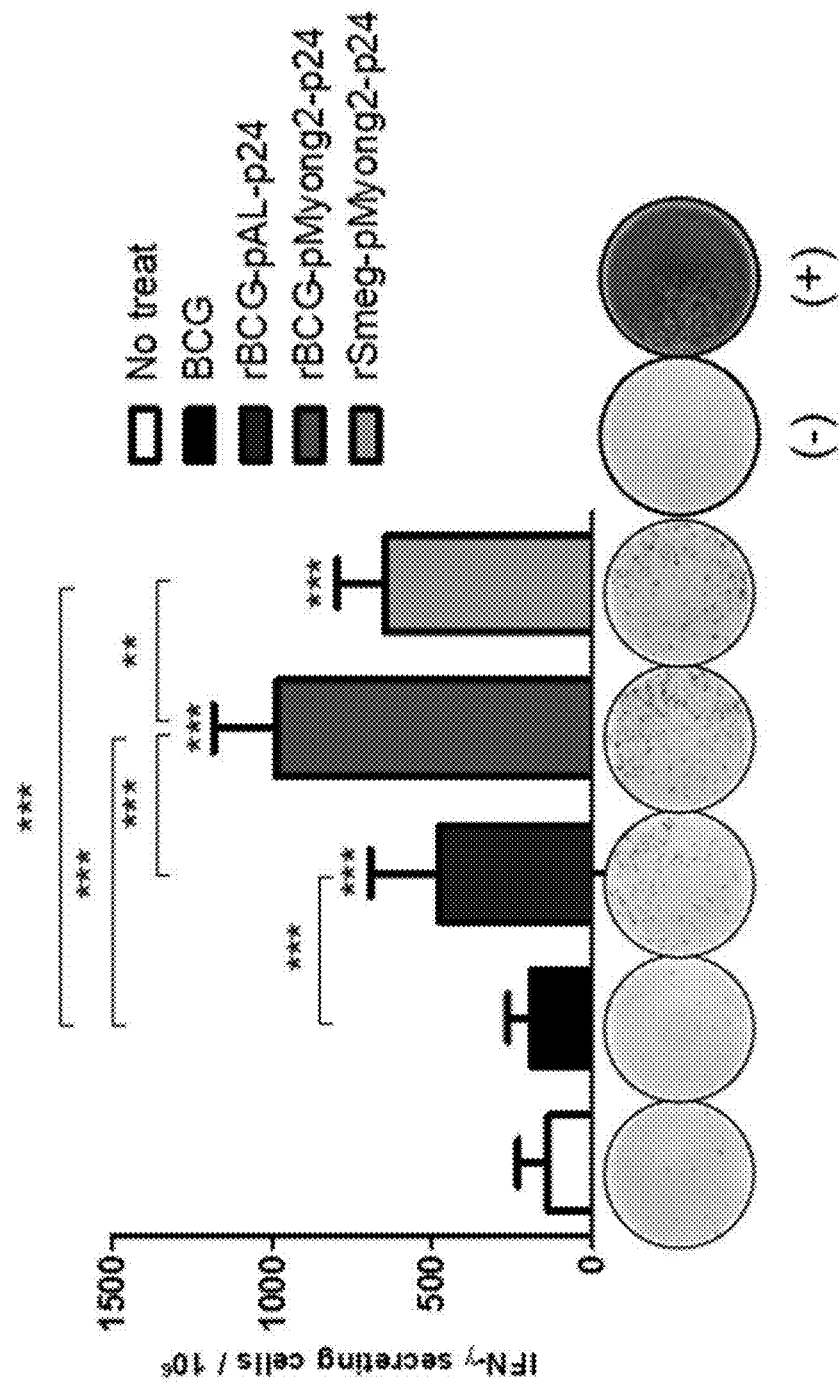
Figure 5C:
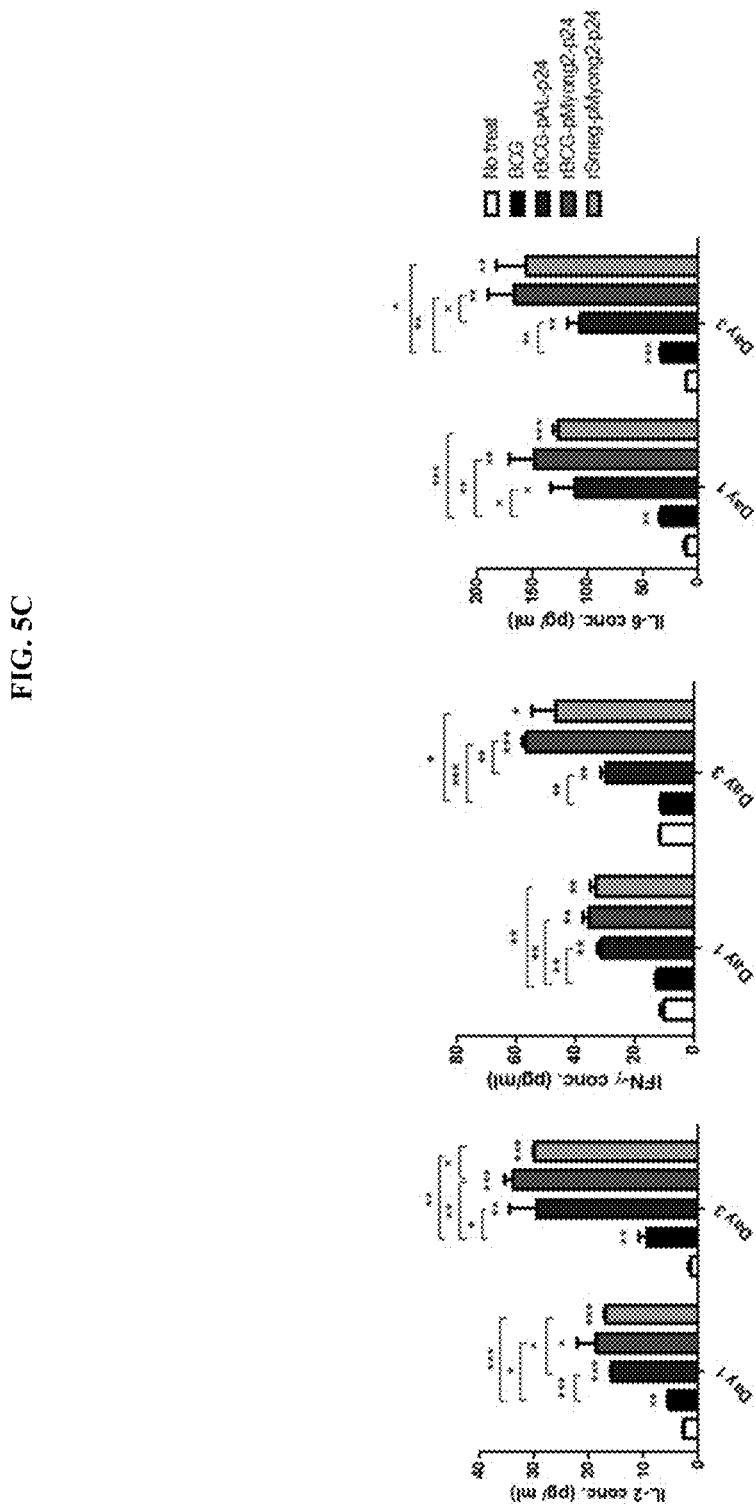
Figure 6:
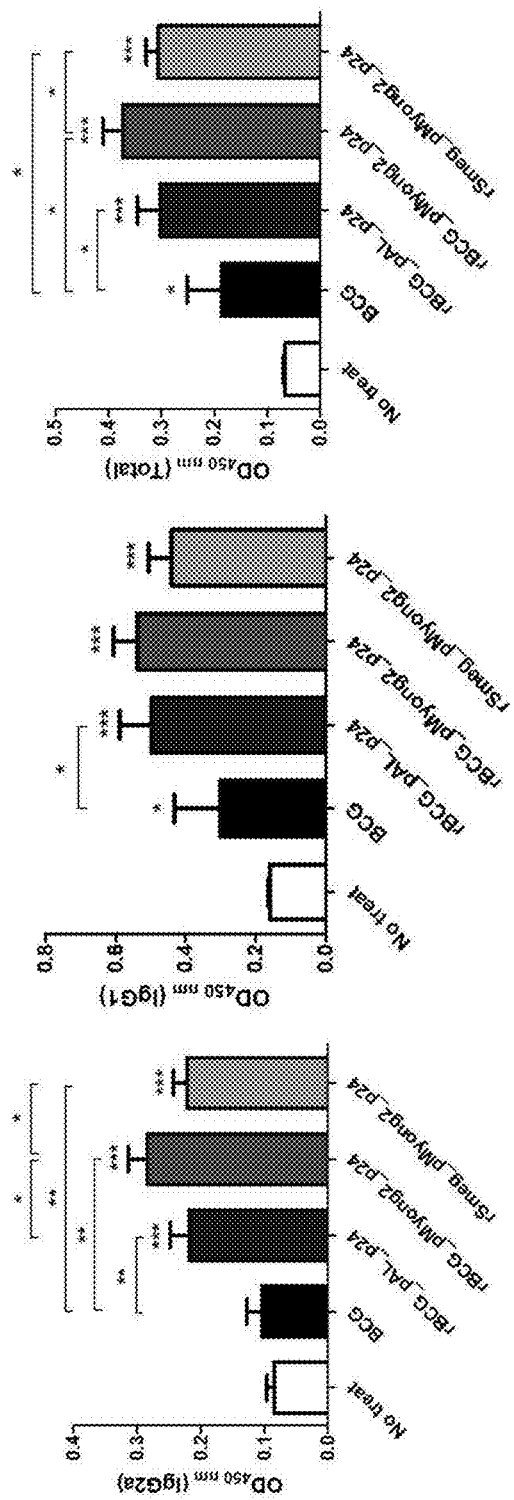

In the present invention, it was confirmed that, by comparison, in rBCG-pMyong2-p24-infected microphages and BMDCs, more p24 protein was produced than in an episomal pAL5000 vector (rBCG-pAL-p24) and an integrative pMV306 vector (rBCG-pMV306-p24) in the related art (FIGS. 3A, 3B, and 3H), providing a mechanistic basis of the enhanced virus-specific vaccine efficacy of rBCG-pMyong2-p24, including enhanced p24-specific T cell proliferation of BMDCs (FIGS. 4B and 4C), T cell effector function (FIGS. 5B and 5C), particularly CTLs (FIG. 7), and Th1-biased humoral immune responses (FIG. 6).

In the present invention, it was observed that rBCG-pMyong2-p24, which produced lower levels of a colony-forming unit (CFU) than rBCG-pAL-p24, tended to be more attenuated in macrophage infection (FIG. 2C), which is presumed to be due to the higher number of copies of pMyong2 in rBCG than that in other vector systems. Considering that immunization with lower doses or more attenuated rBCG can reduce risks associated with high-dose cutaneous administration, including adverse local skin reactions, possible association with Th2-type immune responses, or exacerbation of retroviral infections, rBCG-pMyong2-p24 may have additional advantages in HIV vaccine protocols using rBCG.

Figure 3A:
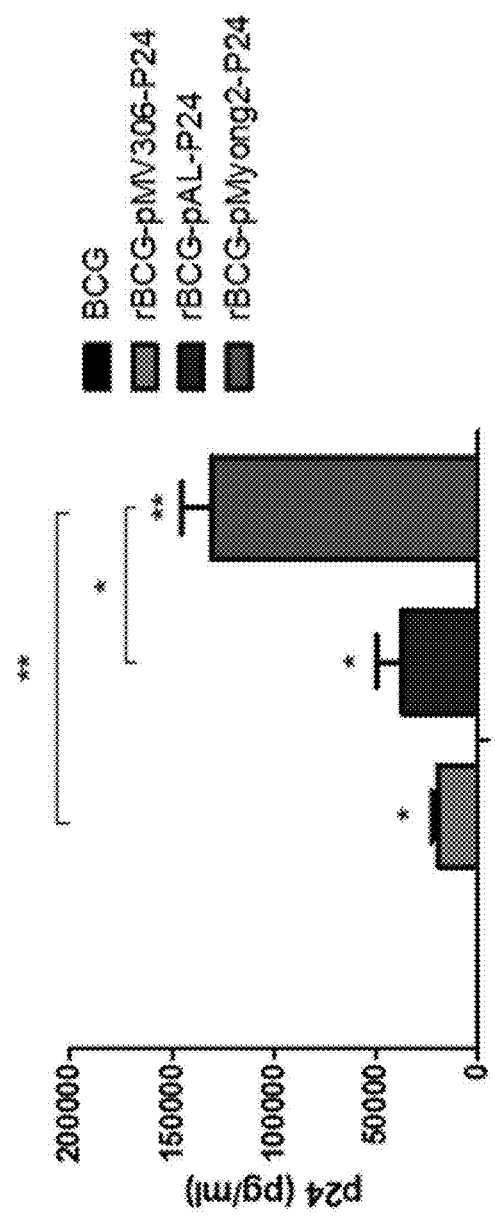
Figure 3B:
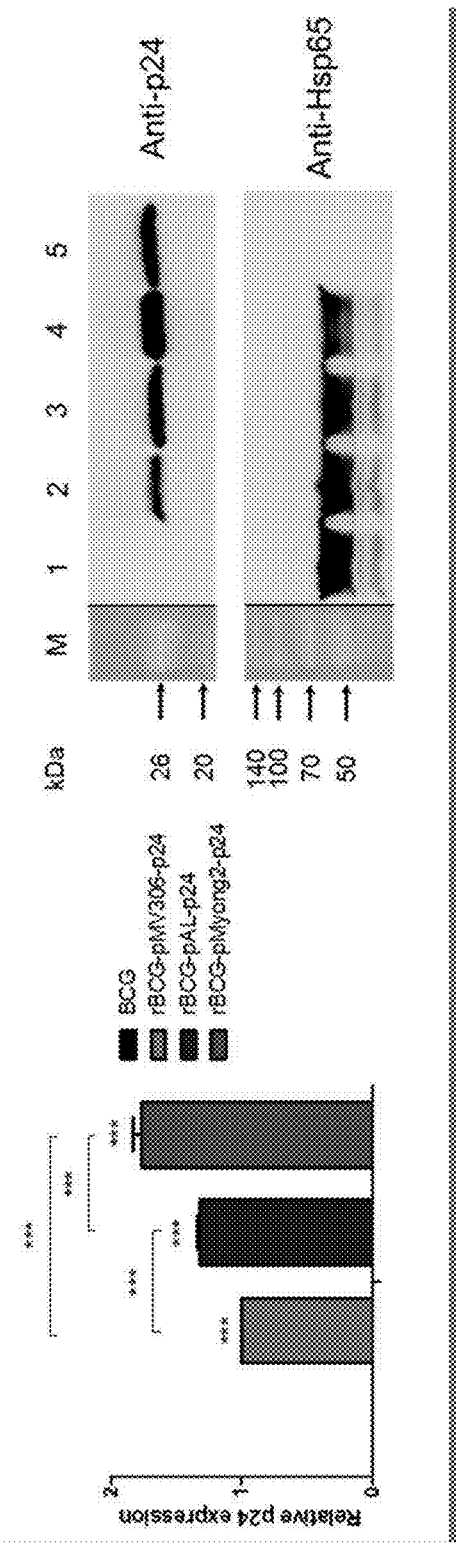
Figure 3C:
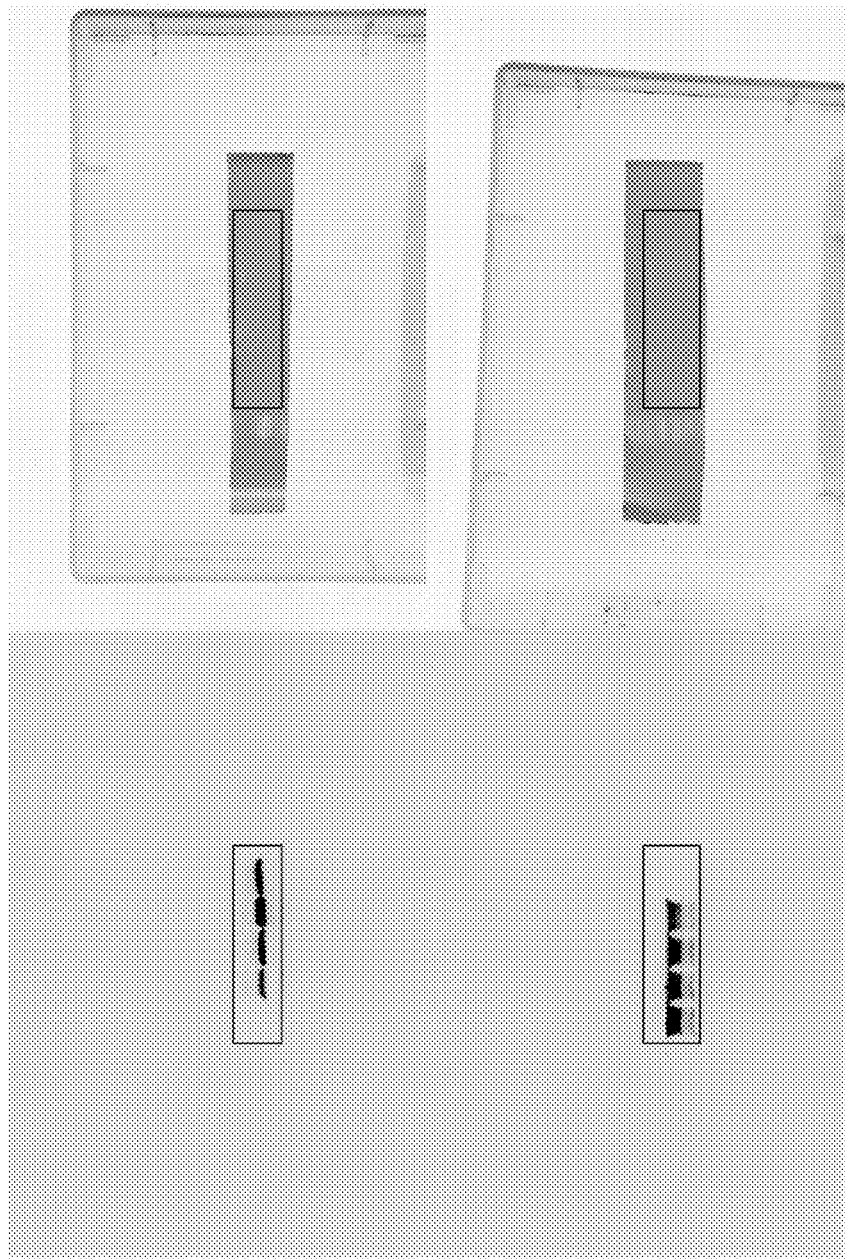
Figure 3D:
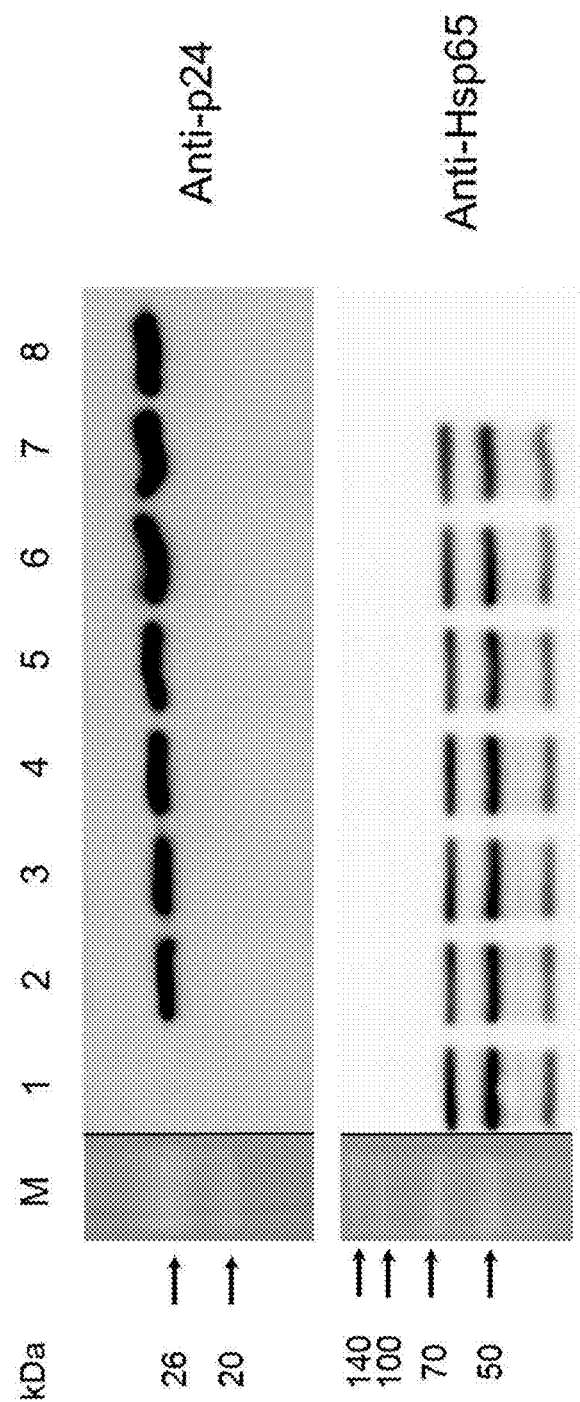

Multi-copy episomal vector-based *mycobacterium-E. coli* shuttle vector systems are known to have drawbacks associated with lack of stability of recombinant *Mycobacterium* compared to integrative plasmid systems. In fact, it was shown that the pMyong2-p24 plasmid gradually lost its stability in rSmeg (rSmeg-pMyong2-p24) after 5 passages in an antibiotic-free medium. However, surprisingly, although the present invention uses the same pMyong2 vector system, the stability of the pMyong2-p24 plasmid in rBCG (rBCG-pMyong2-p24) may be maintained even after 12 passages regardless of whether antibiotics were added (FIG. 3F). This suggests that the pMyong2 plasmid obtained from the slow-growing *Mycobacterium* yongonense may be more stable in slow-growing mycobacteria such as BCG than in rapid growing mycobacteria such as Smeg. Considering that the stability of plasmid incorporation into an antibiotic-free medium is important for the preparation of live recombinant vaccines for practical use, rBCG-pMyong2-p24 has advantages over rSmeg-pMyong2-p24 in application as an HIV-1 vaccine.

In the present invention, in addition to using rBCG strains in different episomal vector systems, that is, rBCG-pMyong2-p24 and rBCG-pAL-p24, the vaccine efficacy against HIV-1 was compared in two different mycobacteria, that is, BCG (rBCG-pMyong2-p24) and Smeg (rSmeg-pMyong2-p24), using the same pMyong2 system. In immune responses against HIV-1 p24 antigens, although the CTL response, T cell proliferation capacity of infected BMDCs and most IFN-γ ELISPOT levels from immunized splenocytes were almost identical in rBCG-pMyong2-p24 and rSmeg-pMyong2-p24, rBCG-pMyong2-p24 showed a significantly enhanced IL-2 production in splenocytes and Th1-biased humoral immune responses compared to rSmeg-pMyong2-p24, suggesting that rBCG-pMyong2-p24 may be superior to rSmeg-pMyong2-p24 in HIV-1 vaccine regimens.

In addition, in the present invention, the vaccine efficacy against HIV-1 was compared between two different vaccine modules, using rBCG-pMyong2-p24 and p24 proteins. The data of the present specification indicates that rBCG-pMyong2-p24 has enhanced p24-specific IFN-γ ELISPOT levels, CTL responses and Th1-biased humoral immune responses, compared to p24 proteins (FIGS. 8A to 8C), also suggesting that rBCG-pMyong2-p24 may be superior to p24 proteins in HIV-1 vaccine regimens. It is known that there is a gender disparity in response to various vaccines, including BCG, measles, mumps and rubella vaccines, and influenza vaccines. In general, in adaptive immune responses, females exhibit enhanced humoral and cell-mediated immune responses, compared to males. This is the reason why only female mice were selected for the current vaccine study in the present invention.

In the present specification, it was demonstrated that rBCG-pMyong2-p24 in the pMyong2 vector system elicited higher levels of HIV-1 p24 Gag protein expression in rBCG and delivered more p24 antigens into phagocytes than the other BCG strains using the pAL5000-(rBCG-pAL-p24) or pMV306-derived system (rBCG-pMV306-p24).

Furthermore, in the present specification, it was shown that the above-mentioned strain could enhance the T cell proliferation capacity of infected BMDCs and induce improved CTL responses and Th1-biased humoral immune responses in vaccinated mice, compared to rBCG-pAL-p24 or rSmeg-pMyong2-p24.

These findings suggest that rBCG-pMyong2-p24 may be an efficient candidate as a prime vaccine in a heterologous prime-boost vaccination strategy for HIV-1 infection.

Taken together, in one aspect, the present invention provides a recombinant *Mycobacterium bovis* BCG (rBCG) expressing a HIV-1-derived p24 protein.

In an exemplary embodiment, the p24 protein may be expressed by the pMyong2-p24 vector system disclosed on FIG. 2A.

In an exemplary embodiment, the p24 protein may be encoded by a Gag gene derived from human immunodeficiency virus type 1 represented by a base sequence of SEQ ID NO: 2.

In an exemplary embodiment, the *Mycobacterium bovis* BCG strain according to the present invention is a Tokyo 172 strain.

Further, the present invention provides an HIV-1 vaccine composition including the recombinant *Mycobacterium bovis* BCG according to the present invention as an active ingredient.

In addition, the present invention provides a method for treating or preventing AIDS and/or tuberculosis by administering, to an individual, a vaccine composition including a therapeutically effective amount of the recombinant *Mycobacterium bovis* BCG according to the present invention as an active ingredient.

Furthermore, the present invention provides a use of the recombinant *Mycobacterium bovis* BCG for preparing a vaccine for preventing or treating AIDS and/or tuberculosis.

Further, the present invention provides a use of the recombinant *Mycobacterium bovis* BCG for preventing or treating AIDS and/or tuberculosis.

In addition, the present invention provides a vaccine composition for HIV infection or co-infection with HIV and *Mycobacterium tuberculosis*, including the recombinant *Mycobacterium bovis* BCG according to the present invention as an active ingredient.

In an exemplary embodiment, the recombinant *Mycobacterium bovis* BCG is live.

In an exemplary embodiment, the vaccine according to the present invention is not further artificially attenuated.

In an exemplary embodiment, the vaccine according to the present invention may be used as a prime vaccine, particularly in a prime-boost vaccination protocol.

In an exemplary embodiment, the infection may be acquired immune deficiency syndrome (AIDS) or tuberculosis.

Advantageous Effects rBCG-pMyong2-p24 according to the present invention has been shown to elicit enhanced HIV-1p24Gag expression in rBCG and infected antigen-presenting cells (APCs).

In addition, the rBCG-pMyong2-p24 according to the present invention has been shown to induce an improved p24-specific immune response, as verified by high levels of HIV-1 Gag-specific CD4 and CD8 T lymphocyte proliferation, gamma interferon ELISPOT cell induction, antibody production and cytotoxic T lymphocyte (CTL) responses, compared to rBCG-pAL-p24 in a pAL5000-derived vector system.

Furthermore, the rBCG-pMyong2-p24 according to the present invention showed a higher level of p24-specific antibody production than rSmeg-pMyong2-p24 in the same pMyong2 vector system.

In conclusion, the present invention has shown that recombinant BCG expressing p24 using a pMyong2 vector system, that is, rBCG-pMyong2-p24, induces an enhanced immune response against HIV-1 infections. Therefore, rBCG-pMyong2-p24 has the potential as a prime vaccine in a heterologous prime-boost vaccination strategy for HIV-1 infection.

DESCRIPTION OF DRAWINGS

FIG. 1 is a view confirming the purity of p24 protein using polyacrylamide gel electrophoresis (SDS-PAGE) and Coomassie brilliant blue staining. M, molecular weight standard (Elpis Bio, Daejeon, Korea). Lane 1, purified p24 protein (10 μg).

FIG. 2A is a view illustrating the cleavage map of each p24 expression vector disclosed in the present specification. As *mycobacterium-E. coli* shuttle vectors expressing an HIV p24 antigen, pMV306-p24, pALp24 and pMyong2-p24 vectors express p24 under the regulation of an hsp65 promoter derived from *Mycobacterium bovis* BCG, respectively.

FIG. 2B is a view illustrating a growth curve of a p24 rBCG strain in a 7H9 medium supplemented with ADC and 100 μg/ml of kanamycin. In the case of wild-type BCG cultures, kanamycin was excluded from the 7H9 medium. For the growth curve, a culture aliquot was taken at each time point and OD600 was measured.

FIG. 2C is a view comparing and illustrating the CFU levels of the p24 rBCG strains in infections of mouse macrophage J774A.1 (left) and mouse bone marrow-derived dendritic cells (right). The data represents two independent experiments. (The results are shown as mean±variance. $^*P<0.05$; $^{}P<0.01$; $^{*}P<0.001$ (Student's t-test).

FIG. 3A is a view confirming p24 expression in the rBCG strains using ELISA.

FIG. 3B is a view confirming the p24 expression of the rBCG strains using western blotting analysis. Proteins were extracted from wild-type BCG (Lane 1) and rBCG strains (Lane 2: rBCG-pMV306-p24, Lane 3: rBCG-pAL-p24, Lane 4: rBCG-p24). Purified p24 protein was used as a positive control (Lane 5). M, molecular weight standard (Elpis Bio, Daejeon, Korea). Individual membranes are separated by white spaces and marker lanes are separated by black vertical lines. The expression levels of p24 are illustrated in the present drawing, and the western blotting images were cropped from a full-length blot to improve clarity. Full-length blotting images are illustrated in the following FIG. 3C.

FIG. 3C is a view illustrating full-length original blotting images of the cropped images of FIG. 2C. Western blotting was performed using the antibodies illustrated in the present drawing. The cropped parts are shown by a solid line.

FIG. 3D is a view confirming the stability of p24 expression in the rBCG-pMyong2-p24 strain passaged on a 7H10 agar plate containing kanamycin using western blotting. Proteins were extracted from wild-type BCG (Lane 1) and rBCG-pMyong2-p24 strains at their respective passage points (Lane 2: 1st passage, Lane 3: after 4th passage, Lane 4: after 6th passage, Lane 5: after 8th passage, Lane 6: after 10th passage, Lane 7: after 12th passage). Purified p24 protein was used as a positive control (Lane 8). M, molecular weight standard (Elpis Bio, Daejeon, Korea). After a membrane was cut as an internal control from an upper size membrane, p24 was detected using Hsp65 antibody (Abcam). Individual membranes are separated by white spaces and marker lanes are separated by black vertical lines.

Figure 2A:
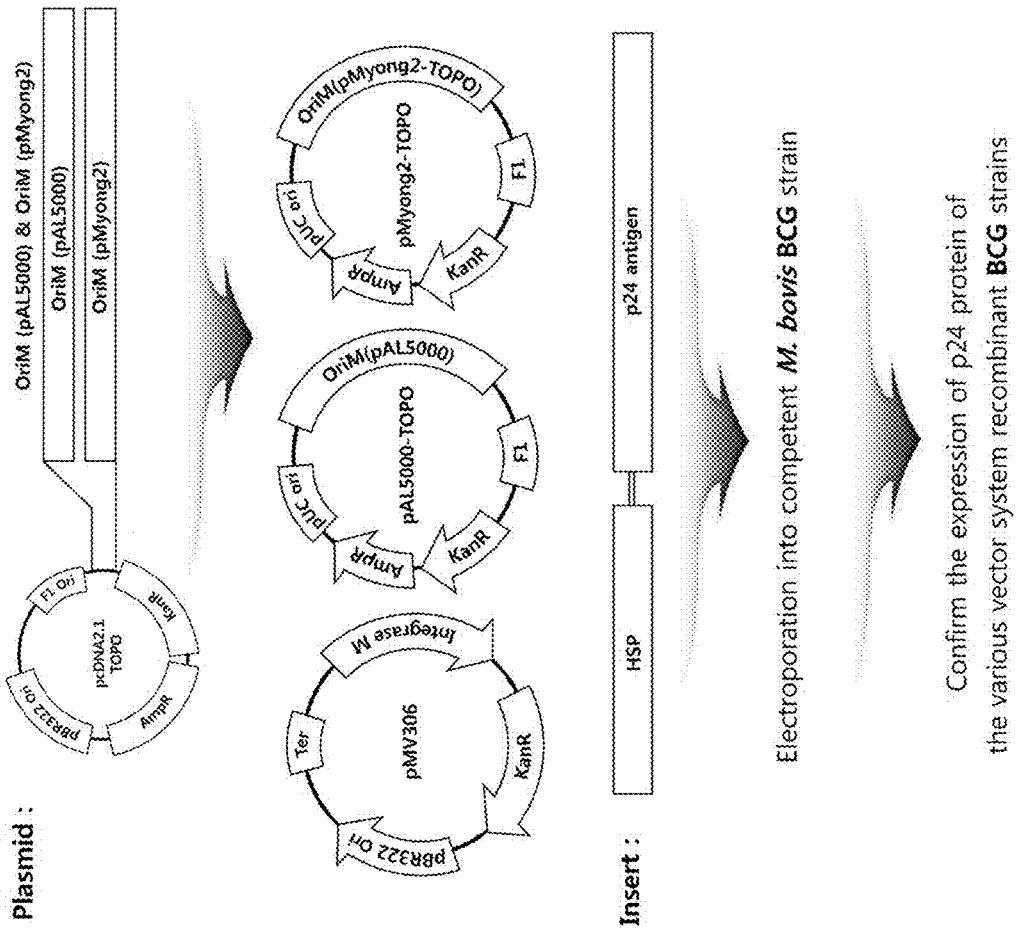
Figure 3E:
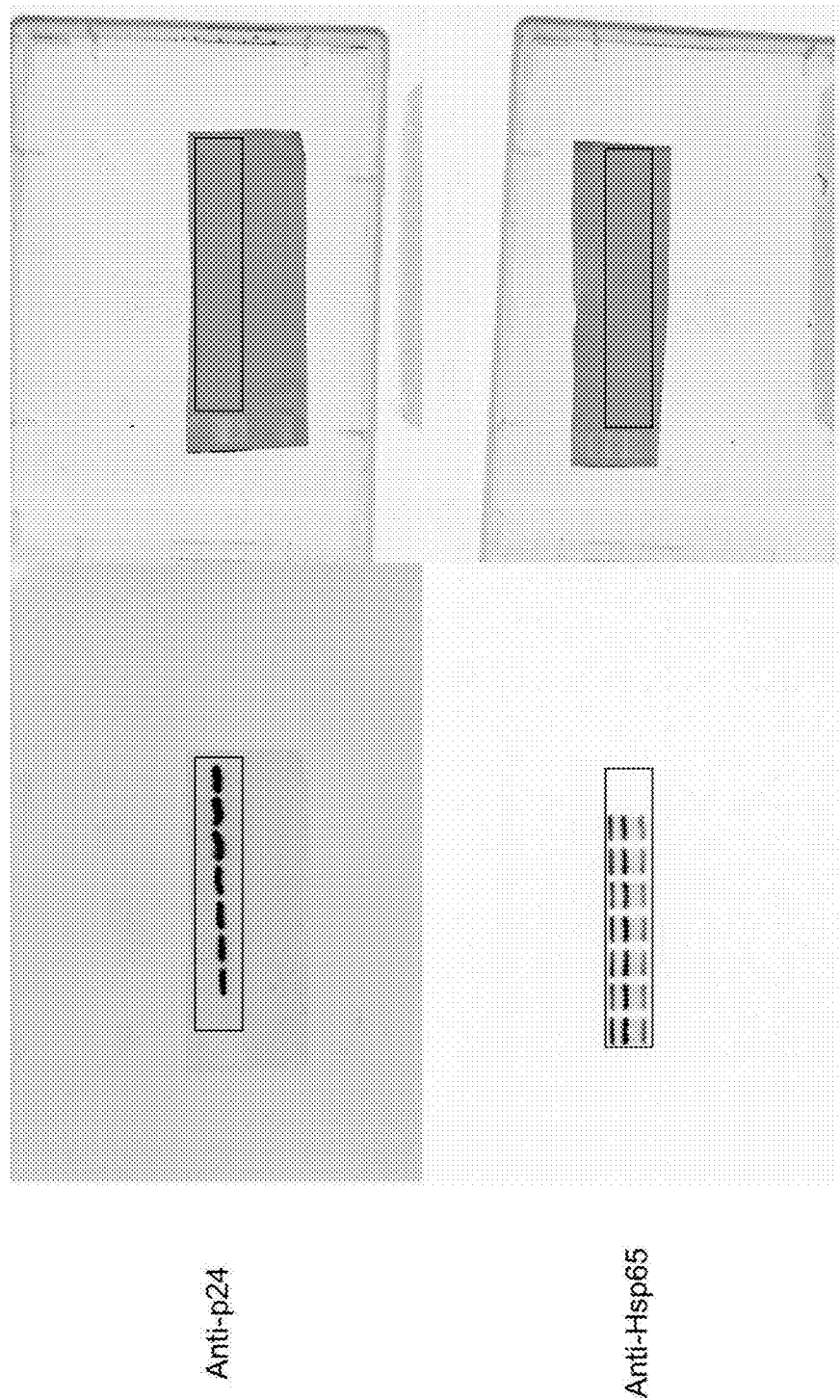
Figure 3F:
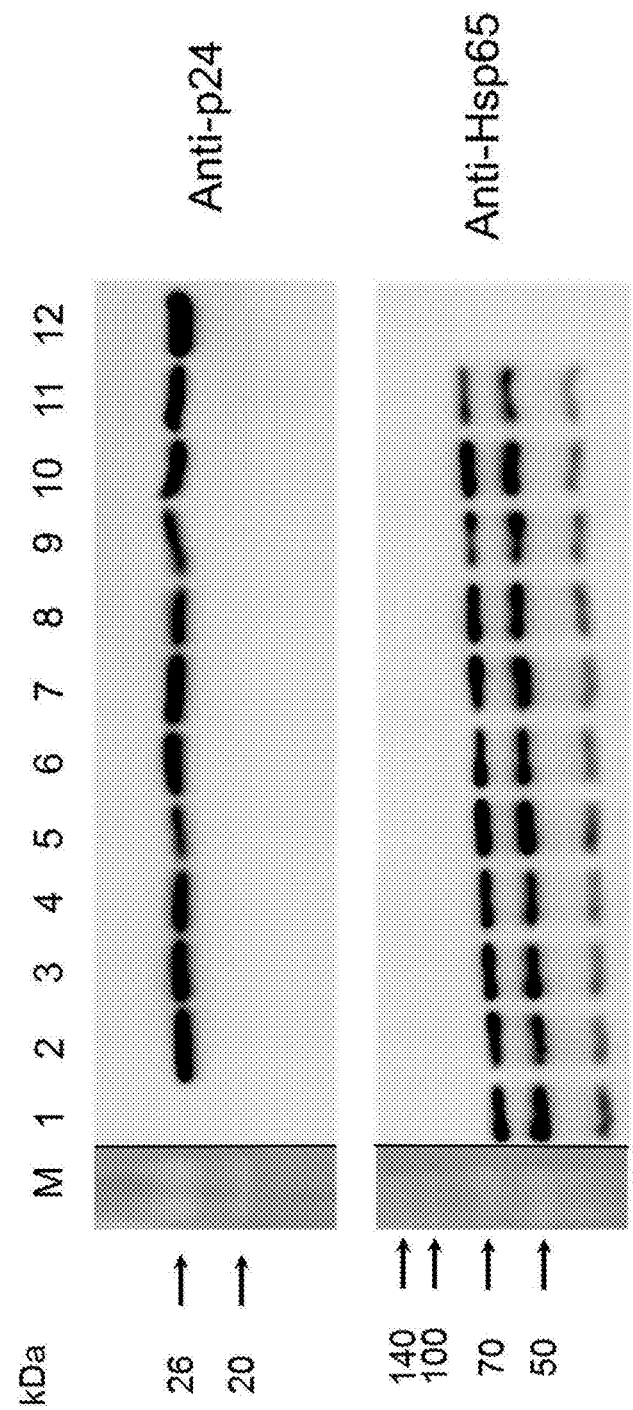

FIG. 3E is a view illustrating full-length original blotting images of the cropped images of FIG. 2D. Western blotting was performed using the antibodies illustrated in the present drawing. The cropped parts are shown by a solid line.

FIG. 3F is a view confirming the stability of p24 expression in the rBCG-pMyong2-p24 strain passaged on a 7H10 agar plate without kanamycin using western blotting. Proteins were extracted from wild-type BCG (Lane 1) and rBCG-pMyong2-p24 strains at their respective passage points (Lane 2: 1st passage, Lane 3: after 4th passage, Lane 4: after 5th passage, Lane 5: after 6th passage, Lane 6: after 7th passage, Lane 7: after 8th passage, Lane 8: after 9th passage, Lane 9: after 10th passage, Lane 10: after 11th passage, Lane 11: after 12th passage). Purified p24 protein was used as a positive control (Lane 12). M, molecular weight standard (Elpis Bio, Daejeon, Korea). After a membrane was cut as an internal control from an upper size membrane, p24 was detected using Hsp65 antibody (Abcam). Individual membranes are separated by white spaces and marker lanes are separated by black vertical lines.

Figure 3G:
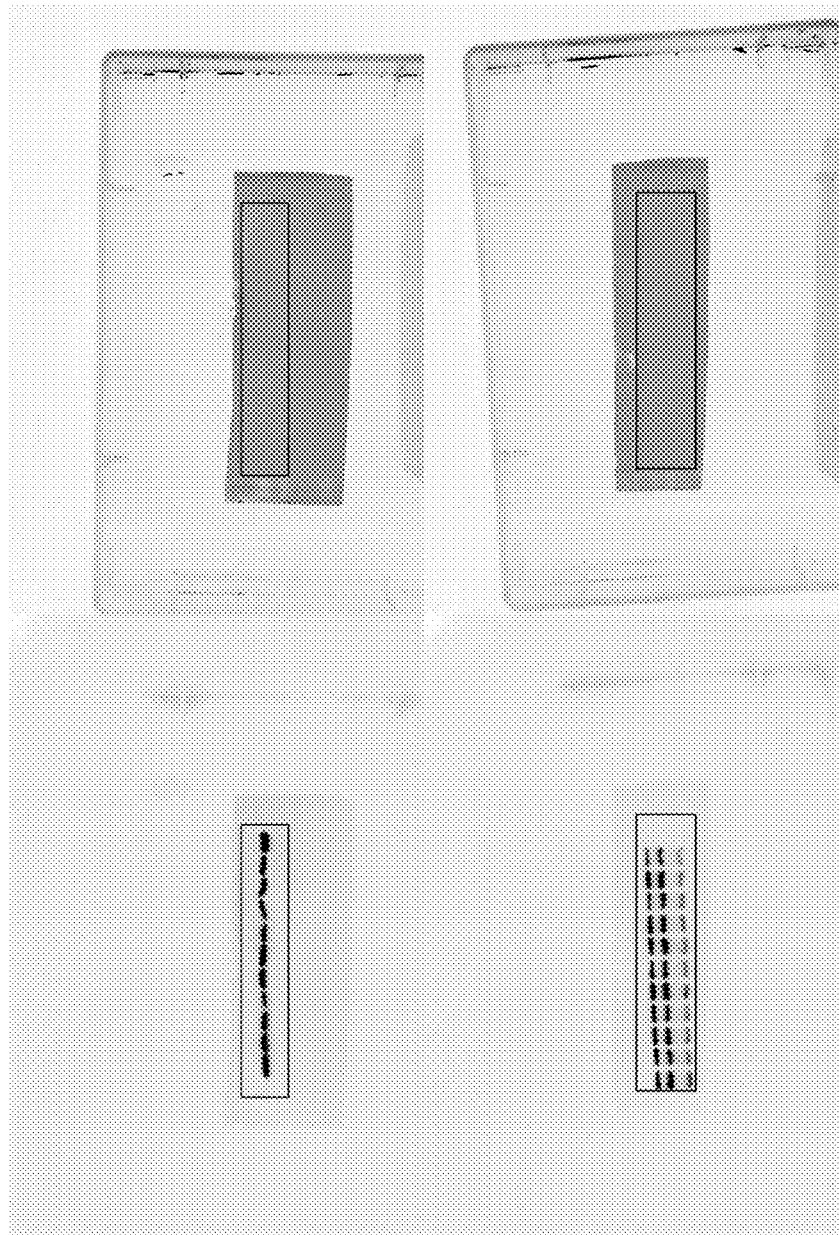

FIG. 3G is a view illustrating full-length original blotting images of the cropped images of FIG. 2F. Western blotting was performed using the antibodies illustrated in the present drawing. The cropped parts are shown by a solid line.

Figure 3H:
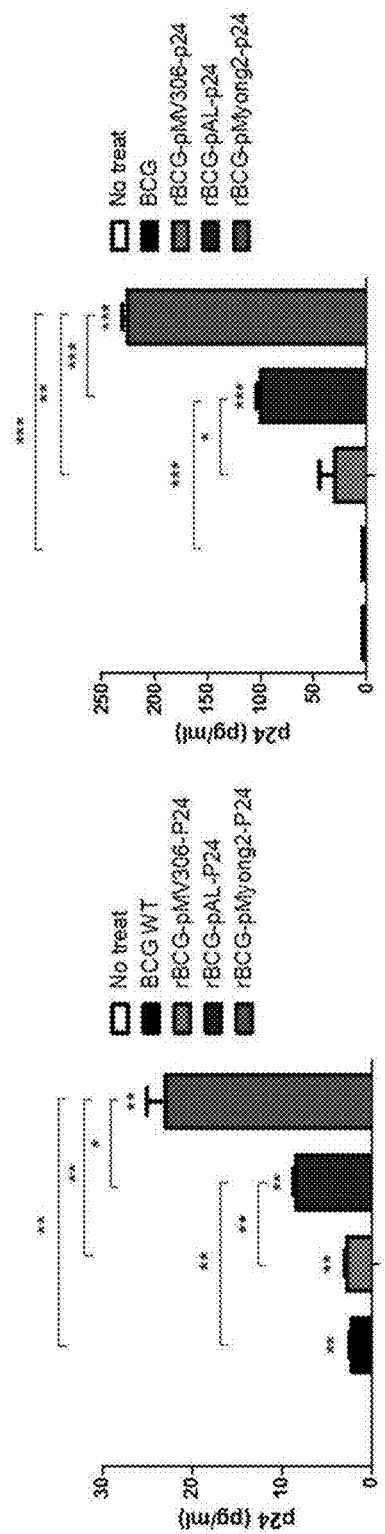

FIG. 3H is a view measuring the expression levels of p24 after infection with wild-type BCG and rBCG strains (rBCG-pMV306-p24, -pAL-p24, and -pMyong2-p24), respectively in mouse microphage J774A.1 (left) and mouse bone marrow-derived dendritic cells (right). The data represents two independent experiments. (The results are shown as mean±variance. *P<0.05; P<0.01; *P<0.001 (Student's t-test).

Figure 3I:
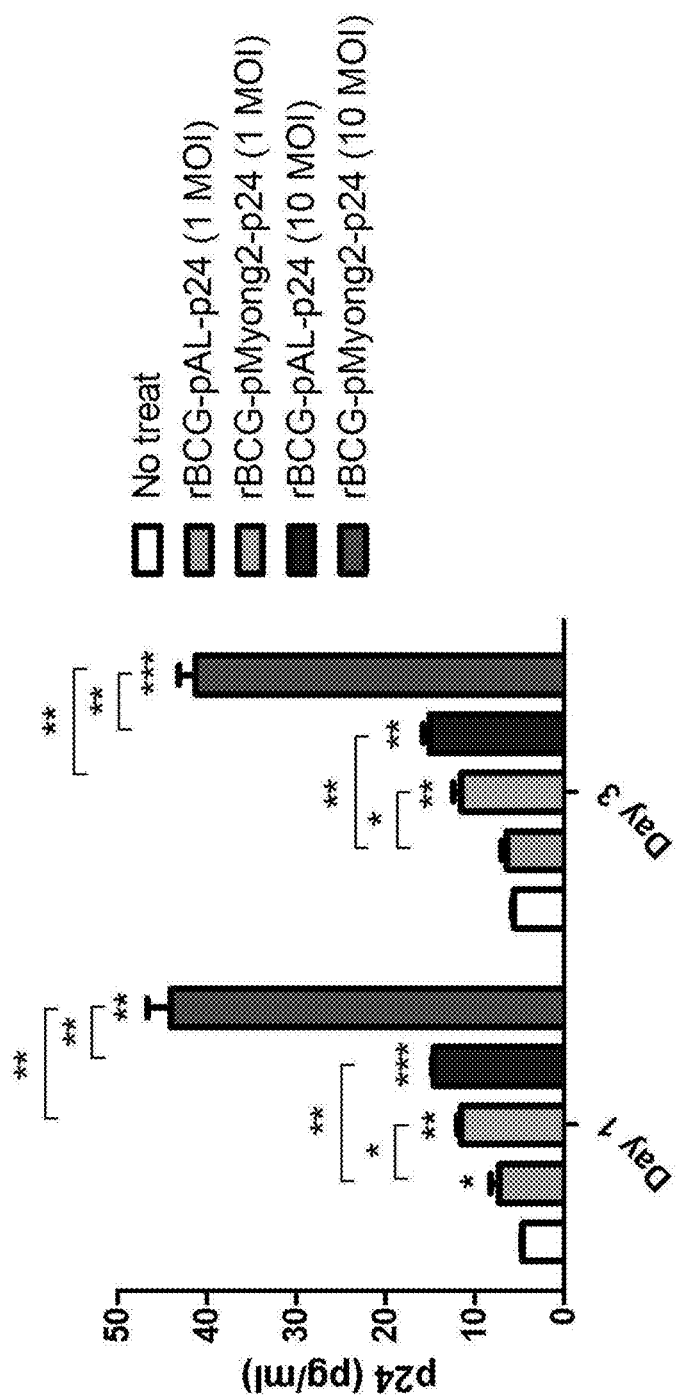

FIG. 3I is a view comparing the expression levels of p24 in BMDCs infected with different M.O.I (1 and 10 M.O.I; multiplicity of infection (M.O.I)) of rBCG-pAL-p24 and rBCG-pMyong2-p24 strains on days 1 and 3 using ELISA. The results are shown as mean±variance in duplicate wells. *P<0.05; P<0.01; *P<0.001 (Student's t-test).

FIGS. 4A to 4D are views illustrating T cell proliferation levels induced by BMDCs infected with p24 rBCG strains. (FIG. 4A) a schematic view of the T cell proliferation analysis schedule. Two mice were injected with the p24 protein (30 μg/mouse), and 7 days later, the splenocytes of the mice were classified into CD4 and CD8T cells and labeled with CFSE. The day before co-culture, DCs were infected with each strain (10 M.O.I). After CFSE-labeled CD4/CD8 T cells and infected DCs were co-cultured for 4 days, the above cells were analyzed for T cell proliferation; (FIGS. 4B and 4C) Results of flow cytometric analysis of CFSE-labeled CD4 and CD8 T cell proliferation of BMDCs infected with p24 rBCG strains (FIG. 4D) ELISA measurement of IL-2 released in supernatants of CD4 (left panel) and CD8 (right panel) cells using MLR analysis. The data represents three independent experiments. The results are shown as mean±variance. *P<0.05; P<0.01; *P<0.001 (Student's t-test).

Figure 5A:
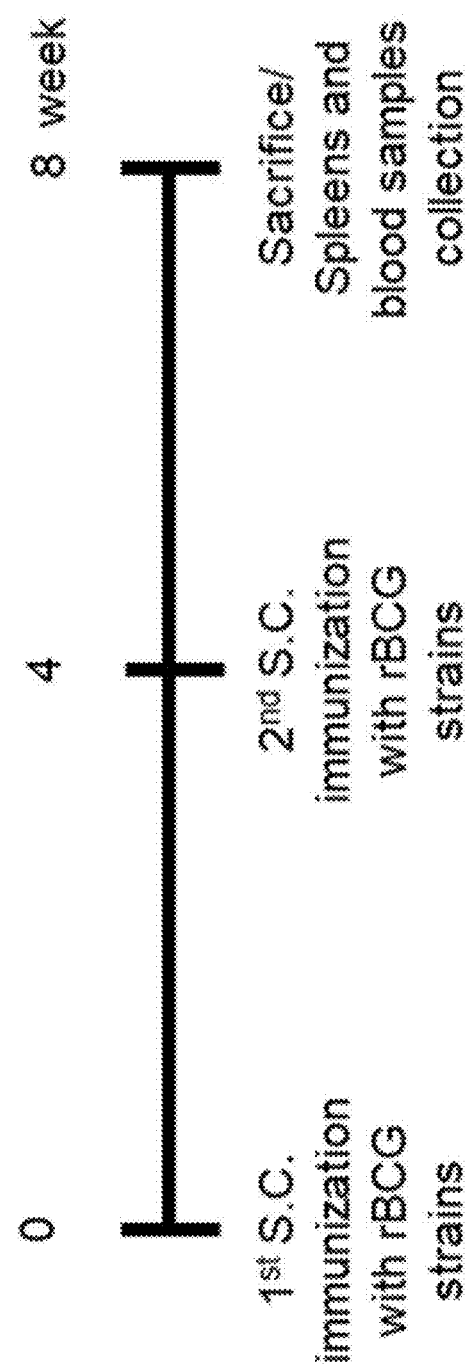

FIGS. 5A to 5C are views illustrating in vivo immune responses induced by p24 rBCG strains, respectively: (FIG. 5A) a schematic view of immunization performed for in vivo immunological analysis. Each group (5 mice/group) was immunized twice with wild-type BCG, two rBCG strains and a rSmeg strain, respectively, at 4 week intervals. 4 weeks after the final immunization, mice were sacrificed and spleens and blood samples were collected for immunoassay; (FIG. 5B) splenocytes of the mice vaccinated with the p24rBCG strains were stimulated in vitro and then detected using IFN-γ secretion level ELISPOT assay. Representative images of ELISPOT membranes of each group are shown below the graph. (−), Negative control; (+), Positive control; (FIG. 5C) After in vitro stimulation of splenocytes of the mice vaccinated with p24 rBCG strains, IL-2, IFN-γ and IL-6 cytokine levels were detected using ELISA assay. A total of 5 mice per group were analyzed. The data represents two independent experiments. The results are shown as mean±variance. *P<0.05; P<0.01; *P<0.001 (Student's t-test).

FIG. 6 is a view illustrating humoral immune responses induced by p24 rBCG strains. The p24-specific immunoglobulin subtypes (IgG2a, IgG1, and total IgG) were measured at 450 nm using ELISA, and the OD values for IgG2a and IgG1 subtypes and the ratios of IgG2a/IgG1 were compared. Serum samples of five mice per group were analyzed. The data represents two independent experiments. The results are shown as mean±variance. *P<0.05; P<0.01; *P<0.001 (Student's t-test).

Figure 7:
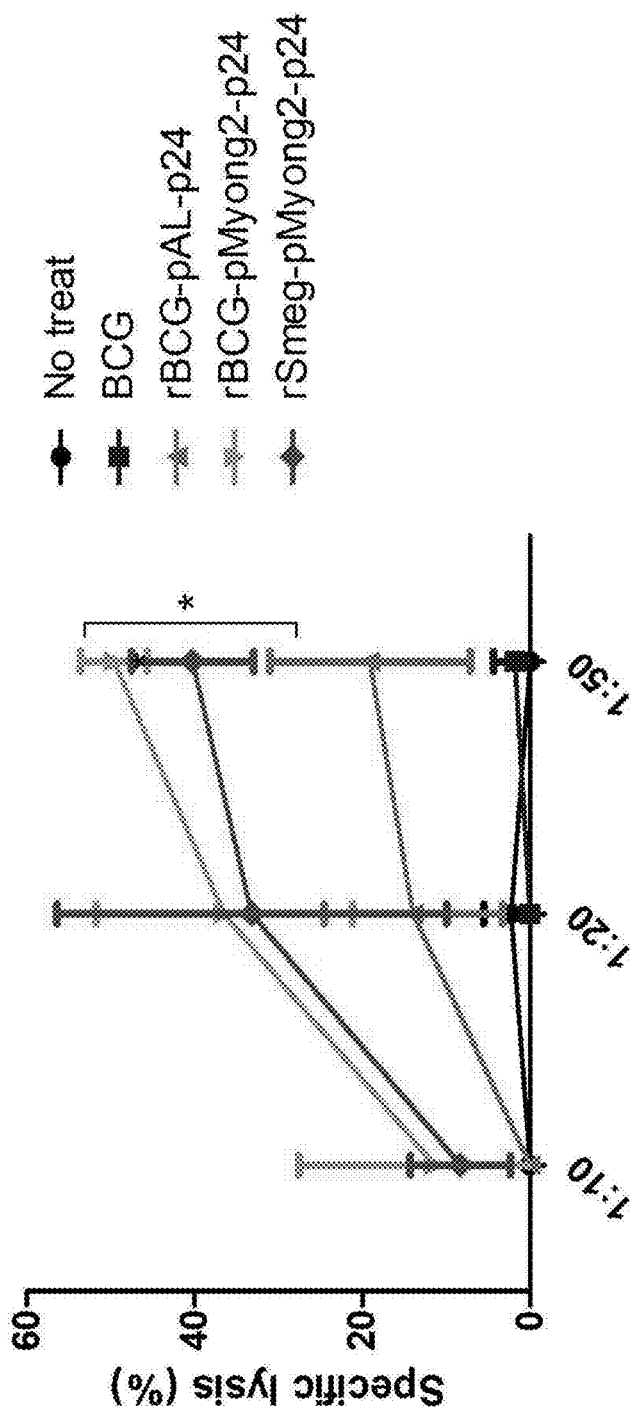

FIG. 7 is a view illustrating the cytotoxic T lymphocyte responses in mice immunized with the rBCG strains. The CTL response occurs when p24-stimulated splenocytes (effector cells) and p24 epitope peptides (A9I) are allowed to react with P815 cells (target cells) in vitro. A total of 3 mice per group were analyzed. The data represents two independent experiments. The results are shown as mean±variance. *P<0.05; P<0.01; *P<0.001 (Student's t-test).

Figure 8A:
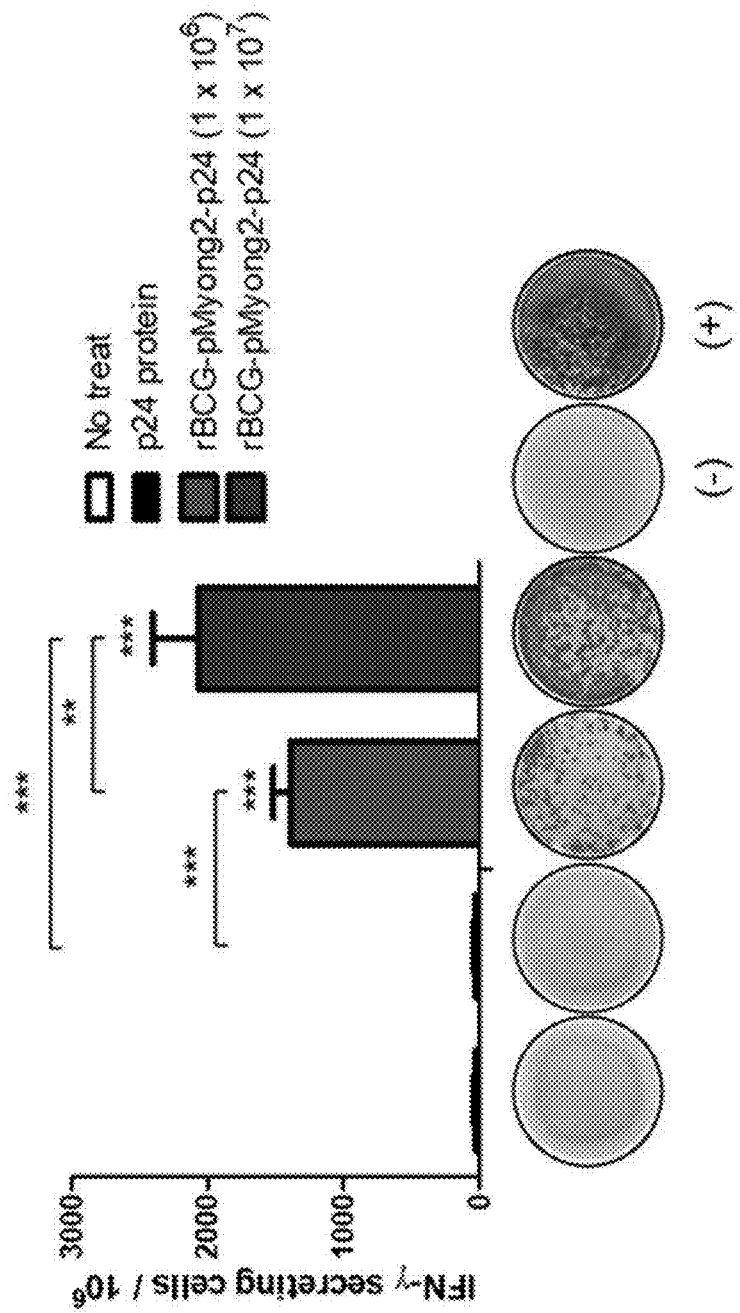
Figure 8B:
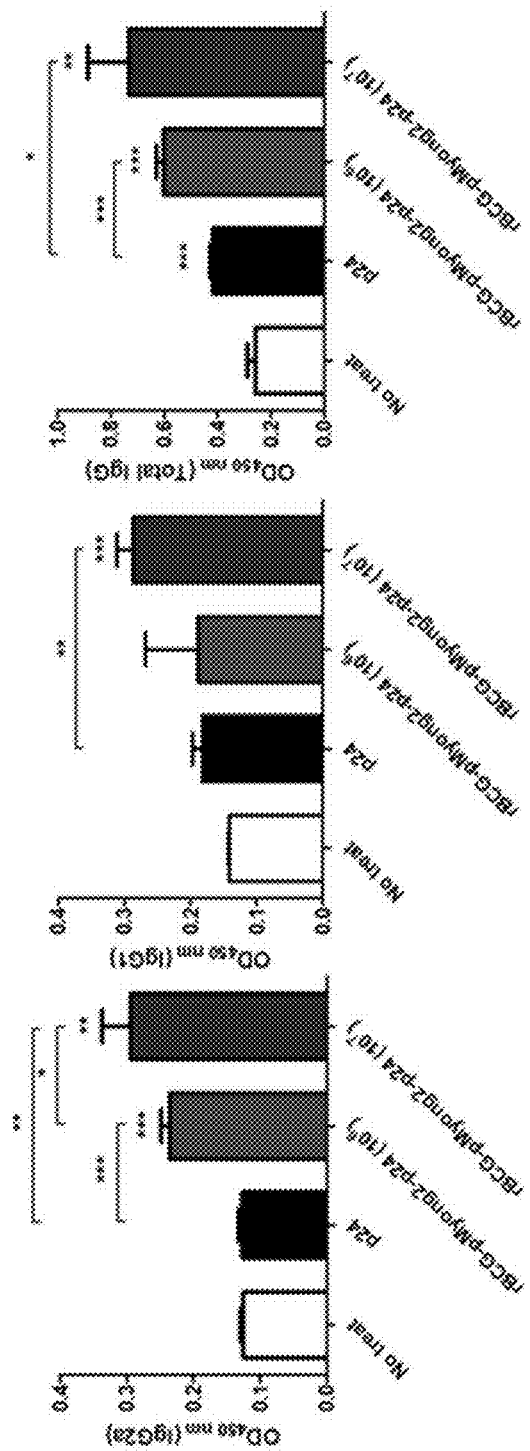
Figure 8C:
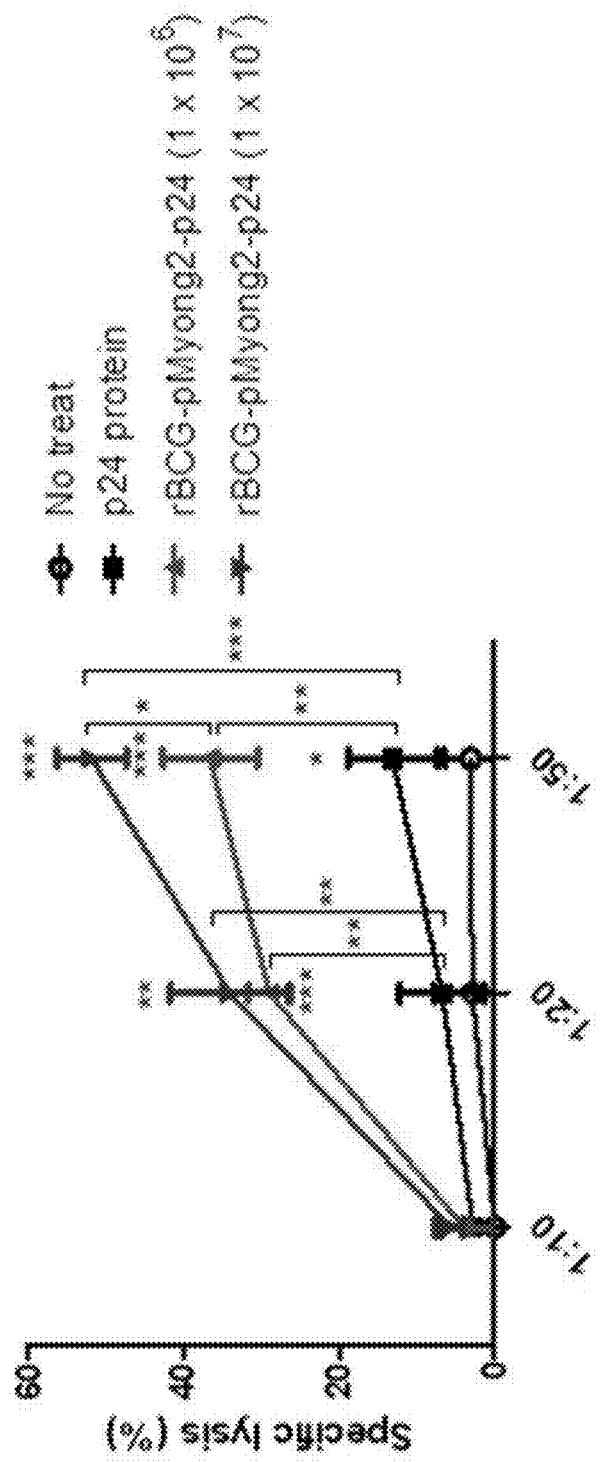

FIGS. 8A to 8C are views illustrating the results of comparison between p24-specific immune responses by injection of the p24 protein and different M.O.I of rBCG-pMyong2-p24 strains. (FIG. 8A) is a set of results of ELISPOT assay for comparing IFN-γ secretion levels after in vitro stimulation of splenocytes obtained from mice hypodermically injected with the p24 protein (30 μg/mouse) and different CFUs ($1\times10^6$ and $1\times10^7$ CFU) of rBCG-pMyong2-p24 strains (1 week intervals, injected twice). Representative images of ELISPOT membranes of each group are shown below the graph. (−), Negative control; (+), Positive control. The results are shown as mean±variance in triplicate. P<0.01; *P<0.001 (Student's t-test); (FIG. 8B) is a set of results of detecting p24-specific immunoglobulin subtypes (IgG2a, IgG1, and total IgG) by ELISA. Serum samples of three mice per group were analyzed. The results are shown as mean±variance in triplicate. P<0.01; *P<0.001 (Student's t-test); (FIG. 8C) is a view illustrating cytotoxic T lymphocyte responses due to the response of splenocytes (stimulated with A9I, p24 epitope peptide; effector cells) obtained from p24 protein- and rBCG-pMyong2-p24 injected mice and A9I peptide-pulsed P815 cells (target cells). Serum samples of three mice per group were analyzed. The results are shown as mean±variance in triplicate. P<0.01; *P<0.001 (Student's t-test).

MODES OF THE INVENTION

The present invention is based on the discovery that recombinant *Mycobacterium bovis* BCG strains expressing the HIV-1 p24 antigen may be effectively used in vaccines.

Thus, in an aspect, the present invention relates to a recombinant *Mycobacterium bovis* BCG strain expressing a p24 protein of HIV-1, and the p24 protein is expressed by the pMyong2-p24 vector disclosed on FIG. 2A.

The p24 capsid (CA) protein expressed by the vector according to the present invention is linked to the 3'-terminus of a matrix protein (MA) in an untreated Gag polyprotein. The p24 capsid (CA) protein includes two domains at the N- and C-termini, which play important roles in HIV budding and capsid structure. The p24 expressed by the vector according to the present invention is derived from HIV-1, the sequence thereof is included in GenBank No. KM390026.1d, or corresponds to an amino acid of SEQ ID NO: 1 or nt 3161 to 3856 of the sequence of SEQ ID NO: 4, and sequence variants thereof may also be used as long as they act as an antigen for the purpose according to the present application. The p24 expressed by a strain according to the present application may act as an antigen against HIV infection when administered to the human body.

In the strain according to the present invention, p24 is expressed by the pMyong2 vector specifically disclosed on FIG. 2A. The recombinant BCG strain including pMyong2-p24 according to the present invention can induce higher levels of HIV-1p24 protein expression and deliver more p24 antigens to macrophages than other rBCG strains using a pAL5000 or pMV306 induction system, so that the recombinant BCG strain is shown to be very excellent.

Furthermore, a BCG recombinant strain including the pMyong2-p24 is shown to be able to improve the T cell proliferation capacity of infected bone marrow-derived dendritic cells (BMDCs) and induce enhanced T cell effector functions and Th1-biased humoral immune responses in vaccinated mice. In addition, a rBCG-pMyong2-p24 strain according to the present application is attenuated due to a delayed initial growth, so that a stronger immune response can be maintained by presenting more antigens to phagocytic cells. These results indicate that rBCG-pMyong2-p24 according to the present invention may be an effective candidate vaccine for HIV-1 or co-infection with HIV-1 and tuberculosis.

Thus, in another aspect, the present invention relates to an immunogenic, vaccine or immunotherapeutic composition for HIV infections including the strains disclosed in the present specification. HIV is a type of retrovirus which destroys the human immune system, and when infected with HIV, HIV progresses to AIDS because the host's immune system is weakened, and the risk of opportunistic infections by bacteria, viruses, fungi, parasites, and the like is remarkably increased. AIDS is acquired immune deficiency syndrome and refers to various symptoms which appear due to a reduction in the immune function of the human body as a result of HIV infection.

The vaccine composition according to the present invention may induce a p24-specific immune response, for example, deliver more p24 antigens to phagocytic cells, improve T cell proliferation capacity, and induce enhanced T cell effector functions and Th1-biased humoral immune responses, so that it is possible to prevent HIV infection or reduce, alleviate, and/or treat symptoms due to the infection.

A vaccine is generally administered twice or more typically in the form of a prime-booster. In this case, the same vaccine is administered several times (homologous), or different types of vaccines including the same antigen are administered (heterologous). In an exemplary embodiment, the vaccine according to the present application is used as a prime vaccine in a homologous or heterologous prime-boost. The rBCG-pMyong2-p24 strain according to the present application has a high expression level of the p24 antigen and a high antigen presenting capacity, so that the rBCG-pMyong2-p24 strain is advantageous for use in prime vaccines because the strain can induce a sufficient p24-specific immune response in naive individuals.

The mycobacteria used in the composition according to the present invention are as described above, and in particular, live viable bacteria may be used. In particular, the rBCG-pMyong2-p24 strain according to the present invention is naturally attenuated due to a delayed initial growth, so that a stronger immune response can be maintained by presenting more antigens to phagocytic cells.

As used herein the term "vaccine" is a biological preparation containing an antigenic material which immunizes the living body, and refers to an immune source which causes immunity in the living body by being infused or injected into an organism for the prevention or treatment of AIDS and/or tuberculosis As used herein, the "individual" refers to a subject in need of treatment of a disease, and more specifically, refers to a mammal such as a human or a non-human primate, a mouse, a rat, a dog, a cat, a horse, and a cow.

As used herein, the "immune response" refers to a response to the introduction of an HIV-1 antigen, for example, a universal HIV-1 antigen through a provided DNA plasmid vaccine, and is used in the present application to mean the activation of the host's immune system, for example, the mammalian immune system. The immune response may be in the form of a cellular or humoral response, or both.

The vaccine composition according to the present invention may be formulated for systemic or topical administration, and may include a pharmaceutically acceptable excipient, carrier and/or vehicle, for example, a phosphate buffered saline solution, distilled water, a water/oil emulsion, a wetting agent, an emulsifying agent, a pH adjusting agent, and the like, but is not limited thereto.

The vaccine composition according to the present invention may include an immunoadjuvant, particularly any material or compound capable of promoting or increasing a T-cell mediated response, if necessary. In an exemplary embodiment, the immunoadjuvant may be used when bacteria which have been killed by chemicals or heat are included in the composition. The immunoadjuvant is known in the art, and it is possible to use, for example, aluminum hydroxide, aluminum phosphate, aluminum potassium sulfate, a crosslinked polyacrylic acid polymer, dimethyldioctadecylammonium bromide (DDA), an immunomodulator, lactoferin, an IFN-gamma derivative, and the like. In an exemplary embodiment, the crosslinked polyacrylic acid polymer includes a Carbopol c homopolymer or copolymer, the lymphokine includes IFNgamma, IL-1, IL-2, or IL-12, and the IFN-gamma derivative may include poly I:C, but is not limited thereto. In an exemplary embodiment, the aluminum hydroxide, aluminum phosphate, or aluminum potassium sulfate, which is a synthesized sugar polymer, is included in an amount of about 0.05 to 0.1 wt %, and the crosslinked polyacrylic acid polymer may be included in an amount of 0.25 wt %, but the amounts are not limited thereto.

The composition according to the present invention may be administered topically or systemically, may be administered once or multiple times, and may be administered by various routes, such as subcutaneously, intradermally, intramuscularly, or intravenously, or may be administered via an oral, nasal or inhalation route. In an exemplary embodiment, the composition according to the present invention is administered once by intramuscular injection.

The vaccine composition according to the present invention may be prepared as a liquid solution or suspension suitable for the route of administration, or may be formulated in a solid form, which is dissolved or suspended in a solution prior to injection.

As used herein, the "therapeutically effective amount" refers to a dose required to induce an antibody that can significantly reduce the probability of infection with human immunodeficiency virus type 1 or the severity of infection. The effective amount is determined by factors including the type and severity of a disease to be treated, the age and sex of a patient, sensitivity to a drug, an administration time, a route of administration, an excretion rate, a treatment period, and drugs to be used together and other factors well known in the pharmaceutical field, is an amount which may obtain the maximum effect without any side effects in consideration of all the above factors and may be easily determined by those skilled in the art.

The dose of vaccine will depend on the patient's age, body weight and/or health status, as well as the route of administration. For example, a suitable dose may be, for example, 1 to $10^9$ CFU. In an exemplary embodiment, $10^6$ CFU is used. In the case of the strain according to the present invention, the expression level of an antigen, the antigen-presenting capacity, and the like are excellent, so it goes without saying that a smaller dose or a smaller dose compared to an existing strain vaccine may be used.

As used herein, the term "prevention" refers to all actions that suppress AIDS and/or tuberculosis or delay the onset of the AIDS and/or tuberculosis by administering the vaccine composition according to the present invention.

As used herein, the term "treatment" refers to all actions that ameliorate or beneficially change symptoms of AIDS and/or tuberculosis by administering the vaccine composition according to the present invention.

In another aspect, the present invention relates to the vector disclosed on FIG. 2A used for the expression of p24 in the strain according to the present invention.

In an exemplary embodiment, the vector is most preferably represented by a base sequence of SEQ ID NO: 4.

In still another aspect, the present invention also relates to cells transformed with the vector. The cells include particularly *Mycobacterium*.

Hereinafter, preferred examples for helping the understanding of the present invention will be suggested. However, the following examples are provided only to more easily understand the present invention, and the contents of the present invention are not limited by the following examples.

EXAMPLES

[Experimental Method]
1. Mice and Immunization Procedures Female BALB/c mice (about 25 g, 7 weeks old) were purchased from Orient-Bio (Seoul, Korea) and used in the experiments at the age of 8 weeks. The mice were randomly divided into 4 groups consisting of 5 mice per group.

For T cell proliferation assay, the p24 protein was injected through the tail vein into 2 mice (BALB/c)(30 μg/mouse), and 5 mice (BALB/c) were used to prepare bone marrow-derived dendritic cells (BMDCs) in each test.

For vaccination test, the BALB/c mice were subcutaneously immunized twice ($1\times10^6$ CFU in 100 μl of PBS; 4 week intervals) at the bottom of the tail with a wild type, two recombinant BCG strains (rBCG-pAL-p24 and rBCG-pMyong2-p24) or a rSmeg-pMyong2-p24 strain. For negative control group, PBS was injected subcutaneously. Four weeks after the final immunization, mice were euthanized by $CO_2$ inhalation at each time point, then blood and spleens of the mice were removed and used for an immunoassay such as IFN-γ ELISPOT, cytokine determination, serum antibody detection (5 mice/group), and CTL analysis (3 mice/group).

Further, independent in vivo tests were conducted to compare differences in immune responses induced by p24 protein treatment and different bacterial numbers. In this case, BALB/c mice (group of 3) were subcutaneously injected twice at one week intervals with the p24 protein (30 μg/mouse) and different numbers of the rBCG-pMyong2-p24 strain ($1\times10^6$ and $1\times10^7$ CFU). For negative control group, PBS was injected subcutaneously. One week after the final immunization, mice were euthanized by $CO_2$ inhalation at each time point, blood and spleens of the mice were removed and used for an immunoassay such as IFN-γ ELISPOT, serum antibody detection, and CTL analysis.

2. Generation of rBCG Strains Expressing HIV-1 p24 Gag

In order to generate three different types of rBCG strains expressing HIV-1 p24 Gag, that is, BCG with the pMyong2-p24 plasmid (rBCG-pMyong2-p24), BCG with the pAL-p24 plasmid (rBCG-pAL-p24), and BCG with the pMV306-p24 plasmid (rBCG-pMV306-p24), three constructed plasmids, that is, pMV306-p24, pAL-p24, and pMyong2-p24 were electroporated into a competent BCG strain (Tokyo 172) using a Gene Pulser II electroporation apparatus (Bio-Rad, Hercules, Calif., USA). Transformants were selected on Middlebrook 7H10 medium (Difco Laboratories, Detroit, Mich., USA) containing kanamycin (100 μg/ml) and OADC. Typically, transformant colonies were selected from plates, transferred to a 7H9 broth medium (Difco Laboratories, Detroit, Mich., USA) supplemented with 0.5% glycerol, 0.05% Tween-80, 10% ADC, and kanamycin, and cultured for 3 to 4 weeks. The growth rate of the rBCG strains was determined by optical density (OD) at 600 nm.

3. Production of p24 Protein from *E. coli*

The recombinant p24 proteins was purified from *E. coli* as previously described with minor modification. For the expression and purification of a fusion protein, *E. coli* BL21 strains (RBC Bioscience, Taipei City, Taiwan) were transformed with pET23a-p24. Protein expression was induced by adding 0.4 mM isopropyl β-d-thiogalactoside (IPTG, Duchefa Biochemie, Haarlem, Netherlands). Bacterial cells were harvested and disrupted by sonication on ice for 10 minutes. The sonicated lysate were centrifuged at 1,600×g at 4° C. for 20 minutes, and pellets containing the p24 protein were resuspended in a binding buffer containing 4 M urea (Sigma Aldrich, St. Louis, Mo., USA). The proteins were purified using a Ni-NTA His binding resin (Merck, Darmstadt, Germany) and eluted with an elution buffer (300 mM NaCl, 50 mM sodium phosphate buffer, 250 mM imidazole) containing 4 M urea. Purified proteins were continuously dialyzed against the elution buffer to remove imidazole, urea, and residual salts. Purity of the p24 protein was estimated by sodium dodecyl sulfate-polyacrylamide gel electrophoresis (SDS-PAGE; 12% gel). The gel was visualized using Coomassie brilliant blue staining methods (FIG. 1).

4. Generation of Bone Marrow-Derived Dendritic Cells from Mice

Bone marrow-derived dendritic cells were generated from the bone marrow (BM) of 8- to 12-week-old BALB/c mice as previously described. Briefly, the BM cells were flushed out of the femur and tibia using a serum-free Iscove's modified Eagle medium (IMDM; Gibco Invitrogen, UK). A single cell suspension was seeded at a concentration of 1×10⁶ cells per well in a 24-well plate in a final volume of 2 ml of complete IMDM supplemented with 10% FBS (Gibco Invitrogen), recombinant mouse GM-CSF (1.5 ng/ml; PeproTech, Rocky Hill, N.J., USA) and mouse IL-4 (1.5 ng/ml; PeproTech, USA), penicillin (100 units/ml; Gibco Invitrogen), streptomycin (100 µg/ml; Gibco Invitrogen), gentamicin (50 µg/ml; Gibco Invitrogen), L-glutamine (2 mM; Gibco Invitrogen), and β-mercaptoethanol (50 nM; Gibco Invitrogen). Half of the medium was replaced every other day with an equal volume of complete IMDM for 6 days. Five mice were used to prepare each experiment using BMDCs, and five 24-well plates were used for differentiating the BMDCs.

5. CFU Assay in Infected J774A.1 and BMDCs with rBCG Strains

A murine macrophage cell line J774.1 (American Type Culture Collection, ATCC, TIB-67) was maintained at 37° C. and 5% $CO_2$ in Dulbecco's modified Eagle's medium (DMEM; Thermo Scientific, Rockford, Ill., USA) supplemented with 10% (v/v) fetal bovine serum (FBS), 2 mM glutamine, and essential amino acids. BMDCs were generated from mouse BM as previously described and maintained at 37° C. and 5% $CO_2$ in Iscove's modified Eagle medium (IMDM; Gibco Invitrogen, UK) supplemented with 10% FBS (Gibco Invitrogen), recombinant mouse GM-CSF (1.5 ng/ml; PeproTech, Rocky Hill, N.J., USA), mouse IL-4 (1.5 ng/ml; PeproTech, USA), penicillin (100 units/ml; Gibco Invitrogen), streptomycin (100 µg/ml; Gibco Invitrogen), gentamicin (50 µg/ml; Gibco Invitrogen), L-glutamine (2 mM; Gibco Invitrogen), and β-mercaptoethanol (50 nM; Gibco Invitrogen).

The J774A.1 cells and BMDCs were infected with the rBCG strains, that is, rBCG-pMyong2-p24, -pAL-p24, and -pMV306-p24 and wild type BCG strains (10 M.O.I) (in triplicate) for 4 hours, followed by three washes with PBS and culturing for 24 hours with fresh media. After 24 hours, the infected cells were lysed with 0.5% Triton X-100. The cell lysate was diluted with PBS and plated onto Middlebrook 7H10 agar plates supplemented with OADC for enumeration of the colony forming units (CFUs). All infected groups were analyzed in triplicate in each experiment, and a total of two independent experiments were conducted.

6. Determination of p24 Gag Expression Levels in rBCG Strains

To determine the p24 Gag expression levels in the rBCG strains, western blot and ELISA analyses were conducted. Briefly, pellets of cultured rBCG strains were suspended in B-PER buffer (Thermo Scientific, Rockford, Ill., USA) supplemented with lysozyme (100 µg/ml), DNase (5 U/ml), and a proteinase inhibitor. Then, the suspensions were sonicated for 5 minutes (pulse: 0.3 second, stop: 0.7 second) on ice and centrifuged at 13,000 rpm at 4° C. for 15 minutes. The same amount of protein in the aqueous phase was used for the western blot analysis. The expression levels of p24 in each rBCG strain were determined using a mouse anti-p24 monoclonal antibody (Abcam, Cambridge, USA; 1:1,000 dilution). Mycobacterial Hsp65 (Abcam, 1:1,000 dilution) was used as an internal control to confirm that the protein concentrations were equal in all samples. To assess the stable expression of p24, the p24 expression levels in the rBCG-pMyong2-p24 strain at various passage points (after 1, 4, 6, 8, 10, and 12 passages) were also determined. The passage process was conducted from plate to plate (7H10 agar plate with or without kanamycin), and the colonies obtained from each passage were cultured in a 7H9 broth medium for 3 weeks, and then each of the experiments was performed. Additionally, the same amount of protein was used for the detection of the p24 levels using a p24 ELISA kit (in triplicate wells) (ABL, Rockville, Md., USA) (as suggested by the manufacturer). All the groups were analyzed in two independent experiments.

7. Determination of p24 Gag Expression Levels in BMDCs and J774.1 Cells Infected with rBCG Strains For the rBCG infection, the J774.1 cells and BMDCs were seeded at 5 to 10×10⁵ cells per well (24-well plate, in triplicate) and cultured for 18 hours. The three different rBCG strains were infected into the cells at a multiplicity of infection (M.O.I) of 10. Also, different M.O.I (1 and 10 M.O.I) of the rBCG-pMyong2-p24 strain was infected into BMDCs to compare the difference in p24 expression by different M.O.I. The J774.1 cells and BMDCs were incubated for 4 hours to allow phagocytosis of the bacteria, and the extracellular bacteria were removed by washing with PBS three times. The infected J774.1 cells and BMDCs were incubated for 24 hours and/or 72 hours.

In order to analyze the p24 expression in the cells, the total proteins in the cell pellets were prepared by suspension in RIPA lysis buffer and used for the determination of the p24 levels using the p24 ELISA kit (ABL) (in triplicate wells) according to the manufacturer's instructions. All the infected groups were analyzed in triplicate in each experiment, and a total of two independent experiments were conducted.

8. T Cell Proliferation Assay

The following experiments were performed for T cell proliferation assay. Two mice were injected intravenously with the p24 protein (30 µg/mouse). After 7 days, the splenocytes were washed with ice-cold FACS buffer [PBS containing 1% bovine serum albumin (BSA) and 1 mM EDTA] and blocked on ice with a super block solution containing 10% rat serum (Sigma Aldrich), 10% goat serum (Gibco Invitrogen), 10% mouse serum (Sigma Aldrich), and 2.4G2 monoclonal antibodies (10 µg/ml; BD Biosciences, San Diego, Calif., USA) for 30 minutes. The cells were subsequently stained with BV421-conjugated anti-CD4 (Clone GK1.5, BD Biosciences) and PE-conjugated anti-CD8a (Clone 53-6.7, eBioscience, San Diego, Calif., USA) at 4° C. for 30 minutes and washed three times with ice-cold FACS buffer. The FACS AriaIII instrument (BD Biosciences) was used to sort the CD4 and CD8 T cell populations. Further, the day before co-culturing, immature BMDCs were infected with the wild type, two rBCGs (rBCG-pMyong2-p24 and -pAL-p24) or rSmeg-pMyong2-p24 strains at an M.O.I of 10 for 24 hours. Proliferation assays were conducted using a fluorescent cytoplasmic tracking dye CFSE (Invitrogen, Carlsbad, Calif., USA). The sorted CD4 and CD8 T cells were stained with 5 µM CFSE at 37° C. for 4 min and on ice for 4 minutes. And then, the CFSE-labeled T cells and infected BMDCs were co-cultured for 4 days.

Figure 4A:
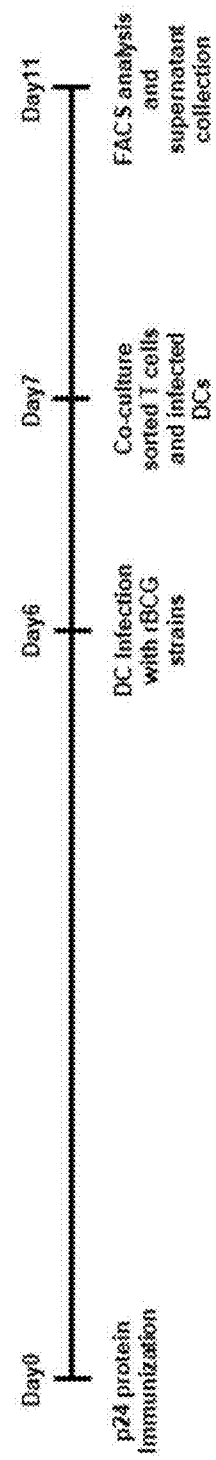

Four days after co-culturing T cells and infected BMDCs, the co-cultured cells (in triplicate wells) were blocked on ice with a super block solution for 30 minutes and stained with CD4 BV421-conjugated anti-CD4 (Clone GK1.5, BD Biosciences) and PE-conjugated anti-CD8a (Clone 53-6.7, eBioscience) at 4° C. for 30 minutes. The cell cycle profiles were determined using FACS LSRFortessa (BD Biosciences) and analyzed using FlowJo software (FIG. 4A). All the experiments were conducted in triplicate.

9. IL-2 ELISA

The amounts of murine IL-2 in the co-cultured supernatants (in triplicate well) from the T cell proliferation assay were determined using ELISA according to the manufacturer's instructions (BioLegend, USA). All the experiments were conducted in duplicate.

10. Enzyme-Linked ImmunoSpot (ELISPOT) Assay

Splenocytes obtained from mice (five mice/group) immunized with wild type and rBCG strains were used to conduct an ELISPOT assay as follows. In brief, 96-well ELISPOT plates (PVDF membrane) were coated with a mouse IFN-γ (3 μg/ml, clone: AN-18) capture antibody (BD-Biosciences, San Diego, Calif., USA) in PBS and incubated at 4° C. overnight. The capture antibody was discarded, and the plates were washed with PBS containing 0.05% Tween-20 (PBST) and PBS (3 times each), and the plates were blocked with 200 μl of RPMI 1640 medium including 10% FBS at 37° C. for 3 hours. After blocking, $5 \times 10^5$ cells of splenocytes from vaccinated mice were loaded into each well. For each treatment group, the cells were stimulated in triplicate with 5 μg/ml of purified p24 antigen or medium alone in a total volume of 200 μl. The plate was incubated at 37° C. for 24 hours. The cells were stimulated with 5 ng/ml of phorbol 12-myristate 13-acetate (PMA) (Sigma-Aldrich, St. Louis, Mo., USA) and 500 ng/ml of ionomycin (Sigma-Aldrich) as a positive control. After washing with PBST and PBS (three times each), each well was treated with the biotin-labeled mouse IFN-γ (3 μg/ml, clone: XMG1.2) detection antibody (BD-Biosciences) and the plate was incubated at 4° C. overnight. The wells were washed again and horseradish peroxidase (HRP)-conjugated streptavidin was added to each well. The HRP reaction was developed using a 3-amino-9-ethylcarbazole substrate reagent set (BD-Biosciences). The number of spot forming units (SFUs) per well was automatically counted using an ELISPOT reader (AID ELISPOT reader, Strasburg, Germany). All the groups were analyzed in triplicate and two independent experiments were conducted.

11. Determination of Cytokine Production in Mice Immunized with rBCG Strains

The splenocytes from the immunized mice (five mice/group) were adjusted to a concentration of $1 \times 10^6$ cells/well (96-well microplate, 200 μl volume, in triplicate) in RPMI 1640 medium including 10% FBS, and purified p24 protein was added at a concentration of 5 μg/ml for the in vitro stimulation. The cells were cultured, and the supernatants were harvested for the IL-2 (BioLegend, San Diego, Calif., USA), IL-6 (eBioscience), and IFN-γ (BioLegend) cytokine determination using ELISA kits. All the groups were analyzed in triplicate and two independent experiments were conducted.

12. Serum Antibody Detection

To detect the serum antibody ratio, serum samples were collected from the immunized mice (five mice/group) using the heart puncture method after euthanasia via hyperventilation of $CO_2$. The 96-well plate was coated with purified p24 protein (5 μg/ml) in a 0.05 M carbonate-bicarbonate buffer (pH 9.6) at 4° C. overnight. The plate was washed three times with PBST and PBS and blocked with 5% bovine serum albumin (BSA in PBST) at room temperature (RT) for 1 hour. The serum samples were diluted at a ratio of 1:10 in PBS and 100 μl was added to each well (in triplicate). The plate was incubated at room temperature for 2 hours, washed three times with PBST and PBS, and incubated with biotinylated rat anti-mouse IgG2a, IgG1 (BD Biosciences, 1:1,000 dilution), and total IgG (eBioscience, 1:1,000 dilution) antibodies for 1 hour. Then, the plate was washed again and incubated with HRP conjugated streptavidin (eBioscience) at room temperature for 30 minutes. After the final washing step, all the wells were reacted with a BD OptEIA substrate (BD Biosciences) for 10 minutes, and then the reaction was stopped using 1 N H2SO4. The optical density (OD) was determined at a wavelength of 450 nm using a spectrometer.

13. Cytotoxic T Lymphocyte (CTL) Assay

The induced CTL responses were determined as previously described with slight modifications. In brief, for the effector cells, the splenocytes obtained from the mice in each immunized group were pulsed using the major histocompatibility complex class I-restricted p24 peptide A9I (AMQMLKETI) (10 μg/ml; Peptron, Daejeon, Korea) and incubated with IL-2 (30 U/ml; PeproTech, Rocky Hill, N.J., USA) at 37° C. in a 5% $CO_2$ incubator for 6 days. The target cells, that is, P815 cells (H-2d), were prepared by an incubation with the A9I peptide (10 μg/ml) for 2 hours followed by a co-culture of the effector and target cells. Cell cytotoxicity was evaluated using a lactate dehydrogenase (LDH) assay in U bottom 96-well plates according to the manufacturer's protocol (CytoTox 96 Non-Radioactive Cytotoxicity Assay; Promega, Madison, Wis., USA). In brief, the effector cells (splenocytes stimulated by antigens) were added to the target cells (p24 pulsed P815 cells) in triplicate at different effector/target (E/T) ratios (ranging from 10:1, 20:1 to 50:1) for 6 hours; then, the values of the LDH released from the cultured supernatants were detected using a spectrometer at 490 nm. The percentage of specific cell lysis was calculated using the following formula: [(Experimental−Effector spontaneous−Target spontaneous)/(Target maximum−Target spontaneous)]×100(%). All the groups were analyzed in triplicate and two independent experiments were conducted.

14. Statistical Analysis

All presented data is expressed as the mean±SD. Student's t-test was used to compare the variance using Microsoft Excel software, and the differences were considered statistically significant at probability values less than 0.05.

EXAMPLES

Figure 2B:
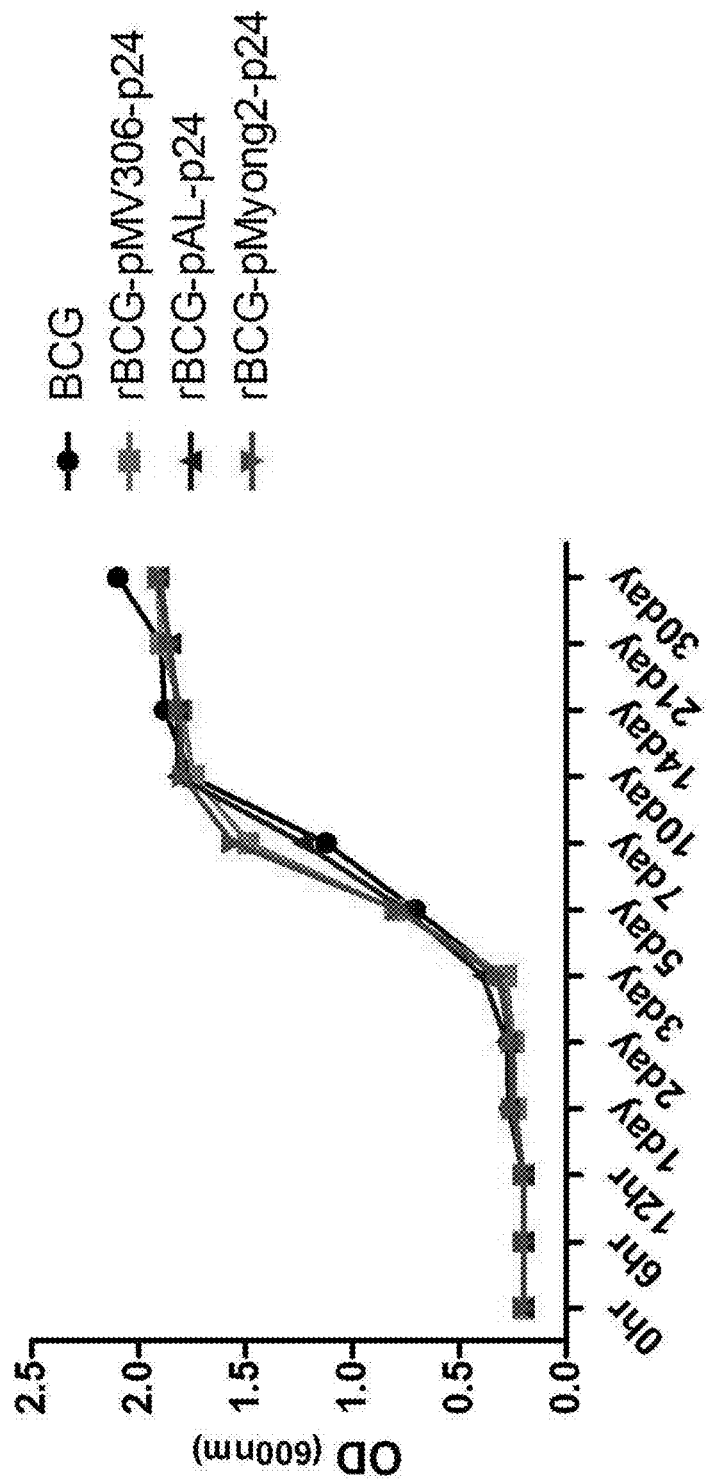
Figure 2C:
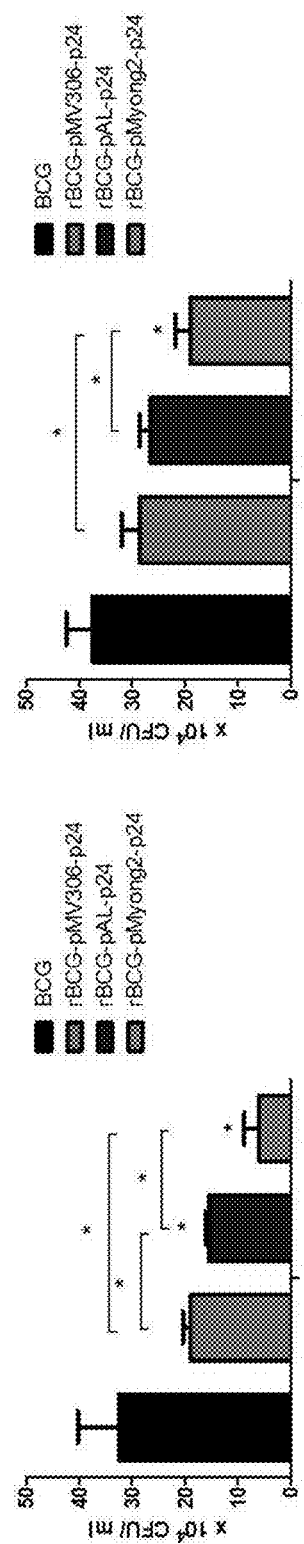

Example 1. rBCG-pMyong2-p24 Strain Elicits Enhanced HIV-1 p24 Gag Expression in Bacteria and Infected Cells In the present invention, to examine the usefulness of a pMyong2 vector system in the preparation of rBCG for HIV-1 p24 Gag vaccination, three types of rBCG strains expressing p24, that is, rBCG-pMyong2-p24, rBCG-pAL-p24, and rBCG-pMV306-p24 were generated using different *Mycobacterium-E. coli* shuttle vectors, that is, pMyong2-TOPO, pAL-TOPO, and pMV306, respectively (FIG. 2A). The growth rates of the three rBCG strains were compared in 7H9 broth (including 100 μg/ml of kanamycin) for 30 days, and as a result, the rBCG and wild-type BCG strains showed a nearly identical growth rate (FIG. 2B). Additionally, to investigate the survival of these rBCG strains in macrophages and DCs, infected cells were lysed with 0.05% Triton X-100 (in PBS) and plated onto 7H10 agar plates. In both cells, the rBCG-pMyong2-p24 strain showed fewer colony forming units (CFUs) than the other strains (that is, rBCG-pAL-p24, -pMV306-p24, and wild-type BCG strains) likely due to the bacterial burden by the enhanced p24 expression (FIG. 2C).

To compare the expression levels of p24 in the bacteria of the three rBCG strains, ELISA (FIG. 3A) and western blot (FIG. 3B) analyses for p24 after lysis of the cultured bacteria were performed. All rBCG strains could express the p24 protein. Similar to the rSmeg-pMyong2-p24 strain, the rBCG-pMyong2-p24 strain expressed approximately 2-fold or 3-fold higher levels of p24 than the strains in the other vector systems. rBCG-pAL-p24 produced a slightly higher level of p24 than rBCG-pMV306-p24 (FIGS. 3A and 3B).

To assess the stable expression of p24, the expression levels of p24 in rBCG-pMyong2-p24 at various passage points on 7H10 agar plates with or without kanamycin were also determined by western blot analyses. The rBCG-pMyong2-p24 strain showed stable p24 expression even after 12 passages on the 7H10 agar plates with or without kanamycin (FIGS. 3D and 3F). Additionally, the expression levels of p24 in murine macrophages (J774A.1) and BMDCs infected with three rBCG strains were examined using ELISA. The trends observed were similar to those observed with the lysed rBCG strains (FIG. 3H).

Further, to compare the p24 expression levels according to the different M.O.I, BMDCs were infected with different M.O.I (1 and 10 M.O.I) of rBCG-pAL-p24 and rBCG-pMyong2-p24 for 1 and 3 days. The results showed that an increased M.O.I of both strains appeared to have an effect of increasing p24 expression. However, as shown above, rBCG-pMyong2-p24 induced more p24 expression than the rBCG-pAL-p24 strain (FIG. 3I).

Taken together, compared to the other two rBCG strains, that is, rBCG-pAL-p24 and rBCG-pMV306-p24, rBCG-pMyong2-p24 increased the production of p24 in infected antigen-presenting cells and bacteria.

Example 2. BMDCs Infected with rBCG-pMyong2-p24 Strain Elicits Enhanced T Cell Proliferation in Mice Immunized with HIV-1 p24 Gag In the present invention, to determine whether the rBCG-pMyong2-p24 showing enhanced p24 protein production could improve the T cell proliferation capacity, a T cell proliferation assay was conducted in BMDCs infected with four different strains, that is, a wild-type BCG (as a control), two types of rBCGs (rBCG-pMyong2-p24 and rBCG-pAL-p24), and rSmeg-pMyong2-p24, respectively using a CFSE dilution method via a mixed lymphocyte reaction (MLR). The rSmeg-pMyong2-p24 strain was also included to compare the capacity of inducing HIV-1 p24 Gag-specific immune responses between two different species using the same pMyong2 vector system, that is, rBCG-pMyong2-p24 and rSmeg-pMyong2-p24. A schematic of the T cell proliferation assay is illustrated in FIG. 4A.

Figure 4B:
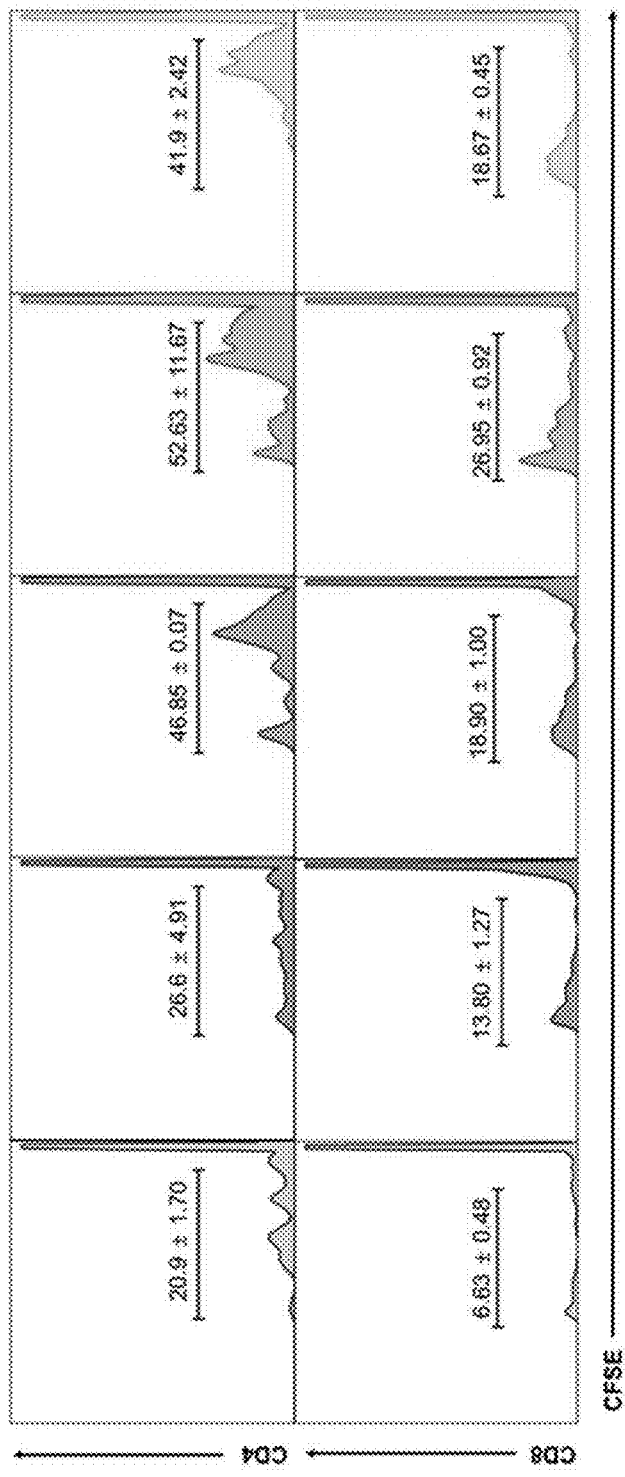
Figure 4C:
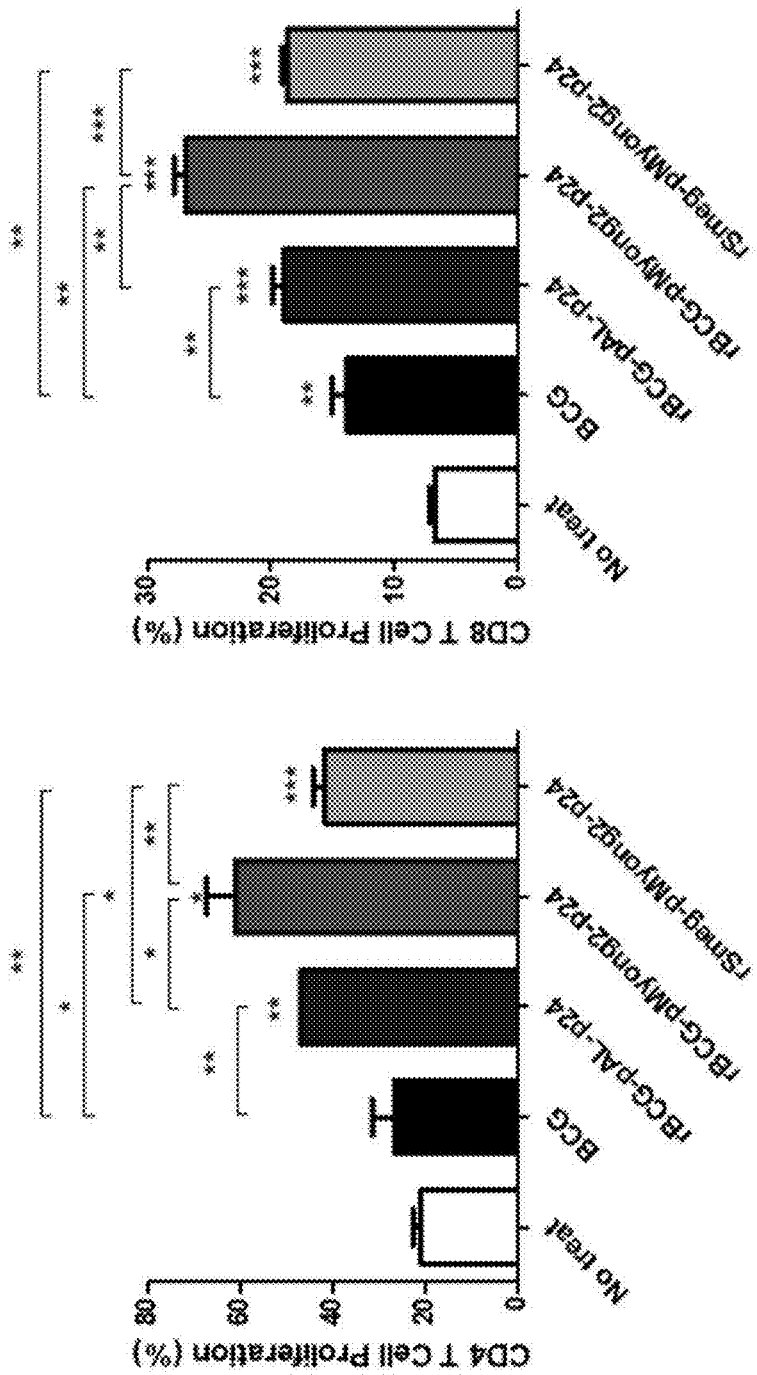
Figure 4D:
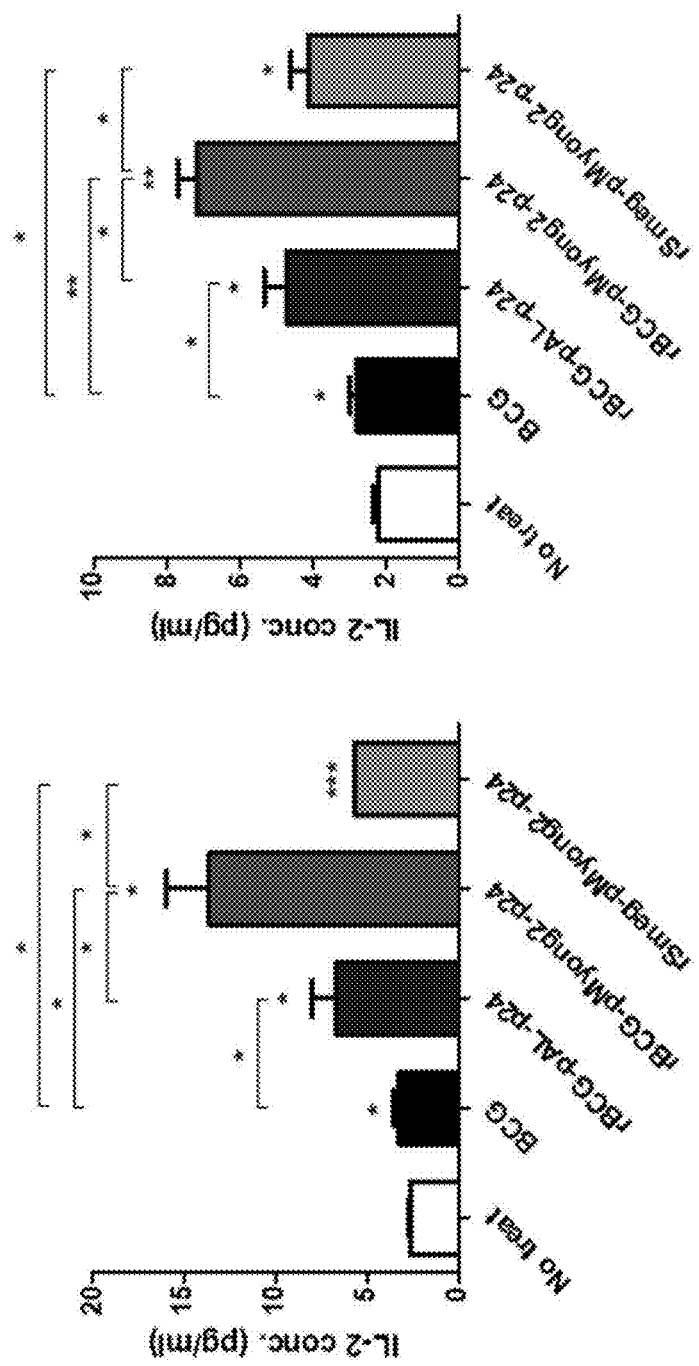

As a result, all BMDCs infected with the two rBCG and one rSmeg strains induced significantly higher levels of CD4 and CD8 T cell proliferation than the BMDCs that were not infected. In particular, the BMDCs infected with rBCG-pMyong2-p24 induced significantly higher levels of CD4 and CD8 T cell proliferation than those infected with the other two recombinant strains (rBCG-pAL-p24 and rSmeg-pMyong2-p24 strains) and the wild-type BCG strain. However, no significant difference in the proliferation of both CD4 and CD8 T cells was observed between the BMDCs infected with rBCG-pAL-p24 and those infected with rSmeg-pMyong2-p24 (FIGS. 4B and 4C). The comparison of the IL-2 levels in stimulated CD4 and CD8 T cells also showed trends that were similar to those observed in T cell proliferation assays (FIG. 4D).

Example 3. rBCG-pMyong2-p24 Strain Elicits Enhanced HIV-1 p24 Gag-Specific IFN-γ Spot Forming Cells (SFCs) in Mouse Spleens Generated by Subcutaneous Immunization To determine whether rBCG-pMyong2-p24 improved the T cell response after vaccination, splenocytes were isolated from the spleens of BALB/c mice (five mice/group) which were subcutaneously immunized with three different strains, that is, two types of rBCG strains (rBCG-pMyong2-p24 and -pAL-p24), rSmeg-pMyong2-p24 (FIG. 4A), and a wild type BCG strain (about $10^6$ CFU) as a control and assayed for HIV-1 p24 Gag-specific T cell responses using IFN-γ ELISPOT assays. The splenocytes from the mice that were subcutaneously immunized with the three recombinant strains showed significantly higher SFUs than those obtained from the mice that were immunized with the wild-type BCG strain. In particular, the splenocytes collected from the mice immunized with rBCG-pMyong2-p24 (987.78±195.11 SFUs/$10^6$ splenocytes) induced significantly higher SFUs than those collected from the mice immunized with the other two strains, that is, rBCG-pAL-p24 (479.56±213.90 SFUs/$10^6$ splenocytes) and rSmeg-pMyong2-p24 (647.00±151.01 SFUs/$10^6$ splenocytes) (FIG. 5B). However, no significant difference was observed between the rBCG-pAL-24 and rSmeg-pMyong2-p24 strains in p24-specific IFN-γ SFUs from vaccinated mice (FIG. 5B).

Taken together, data of the present invention indicated that rBCG-pMyong2-p24 elicited enhanced HIV-1 p24 Gag-specific production of IFN-γ, which is a Th-1 signature cytokine, suggesting its feasibility for enhancing vaccine efficacy by skewing the Th-1 type immune responses.

Example 4. rBCG-pMyong2-p24 Strain Elicits Enhanced Production of Th1 or Pro-Inflammatory Cytokines in Splenocytes Obtained from Vaccinated Mice The splenocytes (five mice/group) obtained 4 weeks after immunization twice with the rBCG strains and rSmeg-pMyong2-p24 (FIG. 5A) were stimulated in vitro in triplicate with purified p24 protein (5 μgimp, and the induced cytokine productions of IL-2, IFN-γ, and IL-6 in the cell culture supernatants were detected. For two Th1 type cytokines, that is, IL-2 and IFN-γ, and one pro-inflammatory cytokine, that is, IL-6, the rBCG-pMyong2-p24 strain produced higher levels of cytokines in splenocytes obtained from vaccinated mice at all time points (day 1 and 3) than the wild type or the other two recombinant strains (FIG. 5C and Table 1).

TABLE 1

| Groups | IL-2 (pg/ml) | | IFN-γ (pg/ml) | | IL-6 (pg/ml) | |
|---|---|---|---|---|---|---|
| | Day 1 | Day 3 | Day 1 | Day 3 | Day 1 | Day 3 |
| No treat | 2.67 ± 0.09 | 1.29 ± 0.37 | 10.02 ± 1.41 | 11.32 ± 0.42 | 10.10 ± 1.16 | 9.92 ± 0.25 |
| BCG | 5.42 ± 0.24 | 9.42 ± 1.44 | 12.55 ± 0.44 | 10.95 ± 0.52 | 32.98 ± 1.91 | 33.22 ± 0.52 |
| rBCG-pAL-p24 | 15.90 ± 0.06 | 29.53 ± 4.90 | 31.31 ± 1.12 | 29.75 ± 1.72 | 111.08 ± 22.47 | 107.28 ± 11.02 |

TABLE 1-continued

| Groups | IL-2 (pg/ml) | | IFN-γ (pg/ml) | | IL-6 (pg/ml) | |
| --- | --- | --- | --- | --- | --- | --- |
| | Day 1 | Day 3 | Day 1 | Day 3 | Day 1 | Day 3 |
| rBCG-pMyong2-p24 | 18.70 ± 3.44 | 33.86 ± 1.38 | 35.38 ± 2.02 | 56.50 ± 1.42 | 148.41 ± 22.76 | 166.26 ± 23.74 |
| rSmeg-pMyong2-p24 | 16.81 ± 0.41 | 29.84 ± 0.37 | 33.15 ± 1.80 | 46.70 ± 8.06 | 126.80 ± 3.76 | 155.76 ± 27.02 |

Example 5. rBCG-pMyong2-p24 Strain Elicits HIV-1 p24 Gag-Specific Th1-Biased Humoral Response in Immunized Mice In the present invention, to determine whether rBCG-pMyong2-p24 elicits a Th1-biased humoral response in immunized mice, the levels of HIV-1 p24 Gag-specific IgG2a and IgG1, which are known markers of Th1 and Th2 responses, respectively, were analyzed. As shown in FIG. 6, the two rBCG and rSmeg-pMyong2-p24 strains elicited significantly higher levels of the IgG2a isotype than the wild type. Regarding the IgG1 isotype, the three recombinant strains induced similar levels of IgG1; however, the result did not reach statistical significance. In the case of total IgG, rBCG-pMyong2-p24 showed significantly higher levels of total IgG than the other two recombinant strains (that is, rBCG-pAL-p24 and rSmeg-pMyong2-p24) (FIG. 6).

Taken together, a higher IgG2a/IgG1 ratio, in which a higher ratio indicates a more Th1-biased humoral immune response, was higher in the sera from the mice immunized with rBCG-pMyong2-p24 (1.03±0.02) than that in the sera from the mice immunized with the other strains (wild-type BCG=0.91±0.71; rBCG-pAL-p24=0.88±0.21; rSmeg-pMyong2-p24=1.01±0.17), and these results show that the rBCG-pMyong2-p24 strain can elicit an enhanced HIV-1 p24 Gag-specific Th1-biased humoral response in immunized mice.

Example 6. rBCG-pMyong2-p24 Strain Elicits Enhanced HIV-1 p24 Gag-Specific Cytotoxic T Lymphocyte Response in Immunized Mice In the present invention, to determine whether rBCG-pMyong2-p24 elicits an enhanced HIV-1 p24 Gag-specific cytotoxic T lymphocyte (CTL) response in immunized mice, the CTL activity in splenocytes from mice immunized with two rBCGs (that is, rBCG-pMyong2-p24 and -pAL-p24), rSmeg-pMyong2-p24, or wild-type BCG strains was evaluated via a LDH cytotoxicity assay. The immunization procedure is described in FIG. 5A. The P815 cells (H-2d) which were pulsed with the A9I peptide for 2 hours were used as the target cells, and the effector/target ratios were 10:1, 20:1, and 50:1 as previously described. As illustrated in FIG. 7, at an E:T ratio of 50:1, the CTLs in the mice immunized with rBCG-pMyong2-p24 could induce a significant higher level of HIV-1 p24 Gag-specific target cell lysis than those immunized with the other strains (FIG. 7). However, no significant difference was observed between the rBCG-pMyong2-p24 and rSmeg-pMyong2-p24 strains (FIG. 7).

Example 7. rBCG-pMyong2-p24 Strain Elicits Enhanced HIV-1 p24 Gag-Specific Humoral and Cell-Mediated Immune Responses in Immunized Mice, Compared to p24 Protein Vaccination In the present invention, to compare the p24-specific immune responses between the p24 protein and different CFUs of rBCG-pMyong2-p24 strains, an independent in vivo experiment was conducted with the following groups: i) PBS control, ii) p24 protein (30 μg/mouse) injection, iii) rBCG-pMyong2-p24 ($1 \times 10^6$ CFU) injection, and iv) rBCG-pMyong2-p24 ($1 \times 10^7$ CFU) injection (1 week intervals, twice subcutaneous injection) groups. The immunization procedure is described in the Experimental Method Section. After the final immunization, p24-specific IFN-γ ELISPOT, IgG subtype analyses, and CTL analyses were conducted. In the case of IFN-γ ELISPOT analysis, the p24-specific IFN-γ SFUs were increased in a CFU-dependent manner. However, splenocytes obtained from the p24 protein injected mice could not induce the p24-specific IFN-γ SFUs (FIG. 8A). Similarly, the p24-specific IgG2a antibodies in serum samples obtained from each immunized mouse were also increased in a CFU-dependent manner. However, the p24-specific IgG2a antibody in serum of the p24 protein injected mice showed lower levels than those of rBCG-pMyong2-p24 injected groups (FIG. 8B).

Also, the p24-specific CTL responses were compared between the p24 protein and different CFUs of the rBCG-pMyong2-p24 strains. The data of the present specification showed that p24-specific CTL responses of rBCG-pMyong2-p24 were increased in a CFU-dependent manner and were always significantly higher than those of the p24 protein (FIG. 8C).

Taken together, the data of the present specification shows that rBCG-pMyong2-p24 can elicit p24-specific Th1-biased cellular and humoral immune responses in a CFU-dependent manner and may have an advantage as an HIV-1 vaccine regimen, compared to a p24 protein vaccination module.

The above-described description of the present invention is provided for illustrative purposes, and those skilled in the art to which the present invention pertains will understand that the present invention can be easily modified into other specific forms without changing the technical spirit or essential features of the present invention. Therefore, it should be understood that the above-described Examples are illustrative only in all aspects and are not restrictive.

The invention claimed is:

1. A recombinant *Mycobacterium bovis* BCG strain expressing the human immunodeficiency virus type 1 (HIV-1) p24 capsid (CA) protein set forth in SEQ ID NO: 1, wherein the p24 protein is expressed by a pMyong2-p24 vector system.

2. The recombinant *Mycobacterium bovis* BCG strain of claim 1, wherein the p24 protein is encoded by a qaq-gene derived from human immunodeficiency virus type 1 represented by a base sequence of SEQ ID NO: 2.

3. The recombinant *Mycobacterium bovis* BCG strain of claim 1, wherein the *Mycobacterium bovis* BCG is a Tokyo 172 strain.

4. An HIV-1 vaccine composition comprising the recombinant *Mycobacterium bovis* BCG strain of claim 1 as an active ingredient.

5. A method of inducing an HIV-1-specific immune response, comprising administering a vaccine composition comprising a therapeutically effective amount of the recombinant *Mycobacterium bovis* BCG strain of claim 1 as an active ingredient to a subject in need thereof.

6. The method of claim 5, wherein the recombinant *Mycobacterium bovis* BCG strain is live.

7. The method of claim 5, wherein the vaccine is not further attenuated.

8. The method of claim 5, wherein the vaccine is used as a prime vaccine in a prime-boost vaccination method.

9. The method of claim 5, wherein the subject has an infection caused by HIV-1 or co-infection caused by HIV-1 and *Mycobacterium tuberculosis*, or the subject is a patient with AIDS or tuberculosis.

* * * * *

SEQUENCE LISTING

<160> NUMBER OF SEQ ID NOS: 4

<210> SEQ ID NO 1
<211> LENGTH: 232

<212> TYPE: PRT
<213> ORGANISM: Artificial Sequence
<220> FEATURE:
<223> OTHER INFORMATION: Amino acid sequence of HIV-1 p24

<400> SEQUENCE: 1

```
Met Pro Ile Val Gln Asn Leu Gln Gly Gln Met Val His Gln Ala Ile
1               5                   10                  15

Ser Pro Arg Thr Leu Asn Ala Trp Val Lys Val Val Glu Glu Lys Ala
            20                  25                  30

Phe Ser Pro Glu Val Ile Pro Met Phe Ser Ala Leu Ser Glu Gly Ala
        35                  40                  45

Thr Pro Gln Asp Leu Asn Thr Met Leu Asn Thr Val Gly Gly His Gln
    50                  55                  60

Ala Ala Met Gln Met Leu Lys Glu Thr Ile Asn Glu Glu Ala Ala Glu
65                  70                  75                  80

Trp Asp Arg Leu His Pro Val His Ala Gly Pro Ile Ala Pro Gly Gln
                85                  90                  95

Met Arg Glu Pro Arg Gly Ser Asp Ile Ala Gly Thr Thr Ser Thr Leu
            100                 105                 110

Gln Glu Gln Ile Gly Trp Met Thr His Asn Pro Pro Ile Pro Val Gly
        115                 120                 125

Glu Ile Tyr Lys Arg Trp Ile Ile Leu Gly Leu Asn Lys Ile Val Arg
    130                 135                 140

Met Tyr Ser Pro Thr Ser Ile Leu Asp Ile Arg Gln Gly Pro Lys Glu
145                 150                 155                 160

Pro Phe Arg Asp Tyr Val Asp Arg Phe Tyr Lys Thr Leu Arg Ala Glu
                165                 170                 175

Gln Ala Ser Gln Glu Val Lys Asn Trp Met Thr Glu Thr Leu Leu Val
            180                 185                 190

Gln Asn Ala Asn Pro Asp Cys Lys Thr Ile Leu Lys Ala Leu Gly Pro
        195                 200                 205

Gly Ala Thr Leu Glu Glu Met Met Thr Ala Cys Gln Gly Val Gly Gly
    210                 215                 220

Pro Gly His Lys Ala Arg Val Leu
225                 230
```

<210> SEQ ID NO 2
<211> LENGTH: 696
<212> TYPE: DNA
<213> ORGANISM: Artificial Sequence
<220> FEATURE:
<223> OTHER INFORMATION: DNA sequence of HIV-1 p24

<400> SEQUENCE: 2

```
atgcctatag tgcagaacct ccaggggcaa atggtacatc aggccatatc acctagaact     60
ttaaatgcat gggtaaaagt agtagaagag aaggctttca gcccagaagt aatacccatg    120
ttttcagcat tatcagaagg agccacccca caagatttaa ataccatgct aaacacagtg    180
gggggacatc aagcagccat gcaaatgtta aaagagacca tcaatgagga agctgcagaa    240
tgggatagat tgcatccagt gcatgcaggg cctattgcac caggccagat gagagaacca    300
aggggaagtg acatagcagg aactactagt acccttcagg aacaaatagg atggatgaca    360
cataatccac ctatcccagt aggagaaatc tataaaagat ggataatcct gggattaaat    420
aaaatagtaa gaatgtatag ccctaccagc attctggaca taagacaagg accaaaggaa    480
ccctttagag actatgtaga ccgattctat aaaactctaa gagccgagca agcttcacaa    540
```

```
gaggtaaaaa attggatgac agaaaccttg ttggtccaaa atgcgaaccc agattgtaag    600
actattttaa aagcattggg accaggagcg acactagaag aaatgatgac agcatgtcag    660
ggagtggggg gacctggcca taaggcaaga gttttg                              696
```

<210> SEQ ID NO 3
<211> LENGTH: 2424
<212> TYPE: PRT
<213> ORGANISM: Artificial Sequence
<220> FEATURE:
<223> OTHER INFORMATION: Amino acid sequence of full vector

<400> SEQUENCE: 3

```
Ala Pro Asn Thr Gln Thr Ala Ser Pro Arg Ala Leu Ala Asp Ser Leu
1               5                   10                  15

Met Gln Leu Ala Arg Gln Val Ser Arg Leu Glu Ser Gly Gln Ala Gln
            20                  25                  30

Arg Asn Cys Glu Leu Ala His Ser Leu Gly Thr Pro Gly Phe Thr Leu
        35                  40                  45

Tyr Ala Ser Gly Ser Tyr Val Val Trp Asn Cys Glu Arg Ile Thr Ile
    50                  55                  60

Ser His Arg Lys Gln Leu Pro Leu Arg Gln Ala Trp Tyr Arg Ala Arg
65                  70                  75                  80

Ile His Arg Pro Pro Val Cys Trp Asn Ser Pro Leu Gly Gly Gln His
                85                  90                  95

Asp Ile Ser Ile Val Gly Thr Glu Leu Leu Asn Asp Asp Ser Pro Ala
            100                 105                 110

Asn Ala Gly Pro Gln Arg Arg Phe Gly Ser Thr Ser Ser Leu Glu Phe
        115                 120                 125

Arg Leu Trp Ser Phe Arg Ser Glu Arg Leu Thr Arg Ser Ala Ser Pro
    130                 135                 140

Val Pro Arg Pro Arg Arg Asp Ser Leu Ala Gly Leu Val Ser Arg Arg
145                 150                 155                 160

Ile Pro Glu Ser Asp Ser Trp Arg Ala Lys Pro Ser His Ile Tyr Arg
                165                 170                 175

Phe Pro Cys Ile Arg Val His Gly Phe Thr Pro Ile Trp Ala Phe Thr
            180                 185                 190

Trp Pro Phe Trp Cys Leu Arg Leu Gly Ser Arg Ser Arg Arg Arg
        195                 200                 205

Val Val Val Thr Thr Ala Phe Asp Ala Ala Glu Ile Ala Ala Ala Val
    210                 215                 220

Pro Glu Ser Gly Ser Pro Cys Ser Gly Thr Ala Ser Ala Arg Leu Arg
225                 230                 235                 240

Arg Ile Arg Ala Lys Glu Ala Arg Arg Ala Ser Ile Glu Arg Cys Gly
                245                 250                 255

Ala Val Pro Ala Ala Val Pro Met Trp Ser Ser Arg Glu Leu Trp Thr
            260                 265                 270

Ala Asp Leu Arg Val Leu Leu Ser Gly Pro Glu Phe Ser Thr Arg Arg
        275                 280                 285

Val Ile Ser Ala Ala Thr Val Leu Ala Val Ala Val Ala Met Ala Glu
    290                 295                 300

Phe Ala Asp His Ala Thr Gly Arg Asn Val Ala Val Thr Asn Glu Val
305                 310                 315                 320

Leu Ala Glu Arg Ala Arg Cys Ser Lys Arg Ser Val Thr Ala Ala Arg
                325                 330                 335
```

```
Gly Val Leu Lys Ala Leu Gly Val Ala Val Glu Ala Val Arg Gly His
            340                 345                 350

Gly Ser Ala Thr Thr His Thr Val Gly Asn Arg Pro Ser Ile Trp His
            355                 360                 365

Leu Val Ser Arg Arg Gln Pro Thr Ile Asp Asn Pro Pro Thr Ala Pro
            370                 375                 380

Gln Asn Gly Arg Gly Glu Pro Ala Asp Thr Val Pro Asp Arg Gly Gln
385                 390                 395                 400

Ser Ala Pro Val Ala Val Glu Thr Cys Asp Leu Pro Ser Arg Arg
                405                 410                 415

Asp Arg Trp Val Thr Pro Val Glu Asn Tyr Ser Pro Ser Thr Arg Glu
            420                 425                 430

Arg Ala Ser Ala Glu Asn Ser Ser Pro Lys Gln Thr Gln Pro Ala Arg
            435                 440                 445

Ser Arg Arg Arg Tyr Arg Ala Thr Pro Arg Pro Leu Asp Val Gln Arg
    450                 455                 460

Leu Ala Ala Gly Leu Val Thr Pro Ala Val Gly His Gly Pro Asp Asn
465                 470                 475                 480

Asp Gly Arg Arg Thr Ala Leu Ile Ala Gly Leu Glu Gln Gly His Ile
                485                 490                 495

Gly Ala Ile Cys Asp Ala Ile Thr Thr Ala Gly Ile Asp Ala Thr Ala
                500                 505                 510

Trp Thr Pro Lys Thr Leu Thr Ala Ala Leu Asn Ala Asp Ala Arg Val
            515                 520                 525

Thr Gly Trp Ser Trp Pro Asp Arg Ile Glu Arg Pro Gly Ala Phe Leu
            530                 535                 540

Ala Ser Arg Leu Arg Arg Leu Pro Ala Arg Pro Asp Thr Ser Gly Pro
545                 550                 555                 560

Val Asp Asn Gly Leu Asp Gln Ala Arg Arg Thr Pro Val Glu Pro Ser
                565                 570                 575

Ala Ala Arg Val Ala Pro Val Gln Thr Ala Ala Gly Arg Ala Tyr Ala
            580                 585                 590

Arg Ala Leu Phe Ala Glu Gln Arg Arg His Arg Val Thr Ala Ala Asn
            595                 600                 605

Ala Gln Ser Ala Ala Val Pro Val Arg Gln Ser Ala Pro Glu Thr Ala
            610                 615                 620

Val Cys Ala Thr Cys Gly Cys Ser Asp Ala Pro Arg Arg Phe Leu
625                 630                 635                 640

Pro Thr Arg Arg Ala His Ile Cys Asp Ala Cys Phe Gln Gly Cys Gly
            645                 650                 655

Gly Gly Gln Ala Arg Thr Gly Arg Val Gly Thr Val Gly Ser Ser Ser
            660                 665                 670

Ala Val Pro Gln Cys Gln Ser Gly Arg Ala Cys Thr Gly Met Arg Thr
            675                 680                 685

His Pro Pro Ala Ala Ala Gly Asp Gly Ser Ser Val Ala Leu Gly Pro
            690                 695                 700

Ser Ser Ser Arg Ala Ser Ser Arg Ser Asp Ala Ile Ser Leu Ala Pro
705                 710                 715                 720

Met Ser Ser Trp Arg Arg Ser His Val Leu Val Met Arg Ser Arg Tyr
                725                 730                 735

Gln Pro Val Gln Ser Ser Pro Val Pro Pro Ala Val Ser Pro Ala Arg
            740                 745                 750
```

-continued

```
Tyr His Ala Ser Arg Arg Ser Arg Pro Arg Ala Trp Leu Met Val Trp
        755                 760                 765
Ala Ala Ala Gln Ser Ala Ser Arg Arg Ala Leu Ser Ala Ser Ser Met
770                 775                 780
Asn Pro Arg Arg Val Met Ser Met Met Ala Gly Asp Gly Ala Ser Gly
785                 790                 795                 800
Pro Gly Met Gly Gly Gly Ser Arg Asn Cys Cys Gly Leu Leu Ala Phe
                805                 810                 815
Ser Ser Ser Ser Cys Trp Trp Val Arg Ser Cys Arg Ala Arg Leu Ser
            820                 825                 830
Arg Tyr Gln Ala Ser Ser Ala Val Arg Gln Ser Pro Pro Val Ala Gly
        835                 840                 845
Ser His Gly Cys Gly Gly Arg Val Val Asn Ser Cys Arg Thr Arg Pro
    850                 855                 860
Ser Met Ser Ser Arg Ser Ser Ser Pro Ala Met Ala Ala Met Arg Ala
865                 870                 875                 880
Gln Pro Gly Arg Trp Leu Arg Gln Ser Ala Gly Ser Ser Pro Leu Arg
                885                 890                 895
Ala His Arg Ser Thr Ser Ala His Asn Pro Arg Ala Asn Ser Ala Asp
            900                 905                 910
Ile Gly Asp His Asn Asp Ala Pro Ala Leu Ile Gly Asp Val Cys Gly
        915                 920                 925
Arg Pro Phe Thr Gly Leu Val Val Gly Gly His Gly Pro Asn Ile
    930                 935                 940
Leu Thr Arg Ile Gly Gly Pro Arg Thr Arg Ser Asn Glu Gly His Asp
945                 950                 955                 960
Pro Val Arg Gly Phe Leu His Ser Ala Ala Ser Ala Lys Asn Asn Val
                965                 970                 975
Gly Thr Arg Asp Arg Val Val Gly Arg Asp Gly Glu Ala Arg Pro Val
            980                 985                 990
Val Ala Ala Ser Gly Ser Glu Asp Asn Leu Ser Arg Pro Ser Arg Ala
        995                 1000                1005
Leu Arg Pro Ala Ser Val Ser Ser Gly Val Ala Val Thr Arg Pro Pro
    1010                1015                1020
Val Ser Ser Pro Ile Arg Arg Asn His Phe Ala Met Pro Ile Val Gln
1025                1030                1035                1040
Asn Leu Gln Gly Gln Met Val His Gln Ala Ile Ser Pro Arg Thr Leu
                1045                1050                1055
Asn Ala Trp Val Lys Val Val Glu Glu Lys Ala Phe Ser Pro Glu Val
            1060                1065                1070
Ile Pro Met Phe Ser Ala Leu Ser Glu Gly Ala Thr Pro Gln Asp Leu
        1075                1080                1085
Asn Thr Met Leu Asn Thr Val Gly Gly His Gln Ala Ala Met Gln Met
    1090                1095                1100
Leu Lys Glu Thr Ile Asn Glu Glu Ala Ala Glu Trp Asp Arg Leu His
1105                1110                1115                1120
Pro Val His Ala Gly Pro Ile Ala Pro Gly Gln Met Arg Glu Pro Arg
                1125                1130                1135
Gly Ser Asp Ile Ala Gly Thr Thr Ser Thr Leu Gln Glu Gln Ile Gly
            1140                1145                1150
Trp Met Thr His Asn Pro Pro Ile Pro Val Gly Glu Ile Tyr Lys Arg
        1155                1160                1165
Trp Ile Ile Leu Gly Leu Asn Lys Ile Val Arg Met Tyr Ser Pro Thr
```

```
                1170                1175                1180
Ser Ile Leu Asp Ile Arg Gln Gly Pro Lys Glu Pro Phe Arg Asp Tyr
1185                1190                1195                1200

Val Asp Arg Phe Tyr Lys Thr Leu Arg Ala Glu Gln Ala Ser Gln Glu
                1205                1210                1215

Val Lys Asn Trp Met Thr Glu Thr Leu Leu Val Gln Asn Ala Asn Pro
                1220                1225                1230

Asp Cys Lys Thr Ile Leu Lys Ala Leu Gly Pro Gly Ala Thr Leu Glu
                1235                1240                1245

Glu Met Met Thr Ala Cys Gln Gly Val Gly Gly Pro Gly His Lys Ala
                1250                1255                1260

Arg Val Leu Ser Arg Gly Pro Asn Ser Pro Tyr Ser Glu Ser Tyr Tyr
1265                1270                1275                1280

Asn Ser Leu Ala Val Val Leu Gln Arg Arg Asp Trp Glu Asn Pro Gly
                1285                1290                1295

Val Thr Gln Leu Asn Arg Leu Ala Ala His Pro Pro Phe Ala Ser Trp
                1300                1305                1310

Arg Asn Ser Glu Glu Ala Arg Thr Asp Arg Pro Ser Gln Gln Leu Arg
                1315                1320                1325

Ser Leu Asn Gly Glu Trp Thr Arg Pro Val Ala Ala His Ala Arg Arg
                1330                1335                1340

Val Trp Trp Leu Arg Ala Ala Pro Leu His Leu Pro Ala Pro Arg Pro
1345                1350                1355                1360

Leu Leu Ser Leu Ser Ser Leu Pro Phe Ser Pro Arg Ser Pro Ala Phe
                1365                1370                1375

Pro Val Lys Leu Ile Gly Gly Ser Leu Gly Ser Asp Leu Val Leu Tyr
                1380                1385                1390

Gly Thr Ser Thr Pro Lys Asn Leu Ile Arg Val Met Val His Val Val
                1395                1400                1405

Gly His Arg Pro Asp Arg Arg Phe Phe Ala Leu Arg Trp Ser Pro Arg
                1410                1415                1420

Ser Leu Ile Val Asp Ser Cys Ser Lys Leu Glu Gln His Ser Thr Leu
1425                1430                1435                1440

Ser Arg Ser Ile Leu Leu Ile Tyr Lys Gly Phe Cys Arg Phe Arg Pro
                1445                1450                1455

Ile Gly Lys Met Ser Phe Asn Lys Asn Leu Thr Arg Ile Leu Thr Lys
                1460                1465                1470

Phe Arg Ala Gln Gly Leu Leu Lys Glu Ala Glu His Val Glu Ser Gln
                1475                1480                1485

Ser Ala Glu Thr Val Leu Thr Pro Asp Glu Cys Gln Leu Leu Gly Tyr
                1490                1495                1500

Leu Asp Lys Gly Lys Arg Lys Arg Lys Glu Lys Ala Gly Ser Leu Gln
1505                1510                1515                1520

Trp Ala Tyr Met Ala Ile Ala Arg Leu Gly Gly Phe Met Asp Ser Lys
                1525                1530                1535

Arg Thr Gly Ile Ala Ser Trp Gly Ala Leu Trp Gly Trp Glu Ala Leu
                1540                1545                1550

Gln Ser Lys Leu Asp Gly Phe Leu Ala Ala Lys Asp Leu Met Ala Gln
                1555                1560                1565

Gly Ile Lys Ile Ser Arg Asp Arg Met Arg Ile Val Ser His Asp Thr
                1570                1575                1580

Arg Trp Ile Ala Arg Arg Phe Ser Gly Arg Leu Gly Gly Glu Ala Ile
1585                1590                1595                1600
```

-continued

```
Arg Leu Leu Gly Thr Thr Asp Asn Arg Leu Leu Cys Arg Arg Val Pro
            1605                1610                1615

Ala Val Ser Ala Gly Ala Pro Gly Ser Phe Cys Gln Asp Arg Pro Val
            1620                1625                1630

Arg Cys Pro Glu Thr Ala Gly Arg Gly Ser Ala Ala Ile Val Ala Gly
            1635                1640                1645

His Asp Gly Arg Ser Leu Arg Ser Cys Ala Arg Arg Cys His Ser Gly
            1650                1655                1660

Lys Gly Leu Ala Ala Ile Gly Arg Ser Ala Gly Ala Gly Ser Pro Val
1665                1670                1675                1680

Ile Pro Pro Cys Ser Cys Arg Glu Ser Ile His His Gly Cys Asn Ala
            1685                1690                1695

Ala Ala Ala Tyr Ala Ser Gly Tyr Leu Pro Ile Arg Pro Pro Ser Glu
            1700                1705                1710

Thr Ser His Arg Ala Ser Thr Tyr Ser Asp Gly Ser Arg Ser Cys Arg
            1715                1720                1725

Ser Gly Ser Gly Arg Arg Ala Ser Gly Ala Arg Ala Ser Arg Thr Val
            1730                1735                1740

Arg Gln Ala Gln Gly Ala His Ala Arg Arg Gly Ser Arg Arg Asp
1745                1750                1755                1760

Pro Trp Arg Cys Leu Leu Ala Glu Tyr His Gly Gly Lys Trp Pro Leu
            1765                1770                1775

Phe Trp Ile His Arg Leu Trp Pro Ala Gly Cys Gly Gly Pro Leu Ser
            1780                1785                1790

Gly His Ser Val Gly Tyr Pro Tyr Cys Arg Ala Trp Arg Arg Met Gly
            1795                1800                1805

Pro Leu Pro Arg Ala Leu Arg Tyr Arg Arg Ser Arg Phe Ala Ala His
            1810                1815                1820

Arg Leu Leu Ser Pro Ser Arg Val Leu Leu Asn Lys Arg Lys Ser Met
1825                1830                1835                1840

Ser Ile Gln His Phe Arg Val Ala Leu Ile Pro Phe Phe Ala Ala Phe
            1845                1850                1855

Cys Leu Pro Val Phe Ala His Pro Glu Thr Leu Val Lys Val Lys Asp
            1860                1865                1870

Ala Glu Asp Gln Leu Gly Ala Arg Val Gly Tyr Ile Glu Leu Asp Leu
            1875                1880                1885

Asn Ser Gly Lys Ile Leu Glu Ser Phe Arg Pro Glu Glu Arg Phe Pro
            1890                1895                1900

Met Met Ser Thr Phe Lys Val Leu Leu Cys Gly Ala Val Leu Ser Arg
1905                1910                1915                1920

Ile Asp Ala Gly Gln Glu Gln Leu Gly Arg Arg Ile His Tyr Ser Gln
            1925                1930                1935

Asn Asp Leu Val Glu Tyr Ser Pro Val Thr Glu Lys His Leu Thr Asp
            1940                1945                1950

Gly Met Thr Val Arg Glu Leu Cys Ser Ala Ala Ile Thr Met Ser Asp
            1955                1960                1965

Asn Thr Ala Ala Asn Leu Leu Leu Thr Thr Ile Gly Gly Pro Lys Glu
            1970                1975                1980

Leu Thr Ala Phe Leu His Asn Met Gly Asp His Val Thr Arg Leu Asp
1985                1990                1995                2000

Arg Trp Glu Pro Glu Leu Asn Glu Ala Ile Pro Asn Asp Glu Arg Asp
            2005                2010                2015
```

```
Thr Thr Met Pro Val Ala Met Ala Thr Thr Leu Arg Lys Leu Leu Thr
                2020                2025                2030

Gly Glu Leu Leu Thr Leu Ala Ser Arg Gln Gln Leu Ile Asp Trp Met
        2035                2040                2045

Glu Ala Asp Lys Val Ala Gly Pro Leu Leu Arg Ser Ala Leu Pro Ala
        2050                2055                2060

Gly Trp Phe Ile Ala Asp Lys Ser Gly Ala Gly Glu Arg Gly Ser Arg
2065                2070                2075                2080

Gly Ile Ile Ala Ala Leu Gly Pro Asp Gly Lys Pro Ser Arg Ile Val
                2085                2090                2095

Val Ile Tyr Thr Thr Gly Ser Gln Ala Thr Met Asp Glu Arg Asn Arg
                2100                2105                2110

Gln Ile Ala Glu Ile Gly Ala Ser Leu Ile Lys His Trp Leu Ser Asp
        2115                2120                2125

Gln Val Tyr Ser Tyr Ile Leu Ile Asp Leu Lys Leu His Phe Phe Lys
        2130                2135                2140

Arg Ile Val Lys Ile Leu Phe Asp Asn Leu Met Thr Lys Ile Pro Arg
2145                2150                2155                2160

Glu Phe Ser Phe His Ala Ser Asp Pro Val Glu Lys Ile Lys Gly Ser
                2165                2170                2175

Ser Asp Pro Phe Phe Leu Arg Val Ile Cys Cys Leu Gln Thr Lys Lys
                2180                2185                2190

Pro Pro Leu Pro Ala Val Val Cys Leu Pro Asp Gln Glu Leu Pro Thr
                2195                2200                2205

Leu Phe Pro Lys Val Thr Gly Phe Ser Arg Ala Gln Ile Pro Asn Thr
        2210                2215                2220

Val Leu Leu Val Pro Leu Gly His His Phe Lys Asn Ser Val Ala Pro
2225                2230                2235                2240

Pro Thr Tyr Leu Ala Leu Leu Ile Leu Leu Pro Val Ala Ala Ala Ser
                2245                2250                2255

Gly Asp Lys Ser Cys Leu Thr Gly Leu Asp Ser Arg Arg Leu Pro Asp
                2260                2265                2270

Lys Ala Gln Arg Ser Gly Thr Gly Gly Ser Cys Thr Gln Pro Ser Leu
        2275                2280                2285

Glu Arg Thr Thr Tyr Thr Glu Leu Arg Tyr Leu Gln Arg Glu Leu Glu
        2290                2295                2300

Ser Ala Thr Leu Pro Glu Gly Arg Lys Ala Asp Arg Tyr Pro Val Ser
2305                2310                2315                2320

Gly Arg Val Gly Thr Gly Glu Arg Thr Arg Glu Leu Pro Gly Gly Asn
                2325                2330                2335

Ala Trp Tyr Leu Tyr Ser Pro Val Gly Phe Arg His Leu Leu Glu Arg
                2340                2345                2350

Arg Phe Leu Cys Ser Ser Gly Gly Arg Ser Leu Trp Lys Asn Ala Ser
        2355                2360                2365

Asn Ala Ala Phe Leu Arg Phe Leu Ala Phe Cys Trp Pro Phe Ala His
        2370                2375                2380

Met Phe Phe Pro Ala Leu Ser Pro Asp Ser Val Asp Asn Arg Ile Thr
2385                2390                2395                2400

Ala Phe Glu Ala Asp Thr Ala Arg Arg Ser Arg Thr Thr Glu Arg Ser
                2405                2410                2415

Glu Ser Val Ser Glu Glu Ala Glu
        2420
```

<210> SEQ ID NO 4
<211> LENGTH: 7445
<212> TYPE: DNA
<213> ORGANISM: Artificial Sequence
<220> FEATURE:
<223> OTHER INFORMATION: DNA sequence of full vector

<400> SEQUENCE: 4

| | | | | | |
|---|---|---|---|---|---|
| agcgcccaat | acgcaaaccg | cctctccccg | cgcgttggcc | gattcattaa tgcagctggc | 60 |
| acgacaggtt | tcccgactgg | aaagcgggca | gtgagcgcaa | cgcaattaat gtgagttagc | 120 |
| tcactcatta | ggcaccccag | gctttacact | ttatgcttcc | ggctcgtatg ttgtgtggaa | 180 |
| ttgtgagcgg | ataacaattt | cacacaggaa | acagctatga | ccatgattac gccaagcttg | 240 |
| gtaccgagct | cggatccact | agtaacggcc | gccagtgtgc | tggaattcgc ccttaggcgg | 300 |
| gcaacacgac | atctcaatag | ttggcacgga | gctcctaaac | gacgacagcc ccgctaatgc | 360 |
| ggggccgcaa | cgtcgatttg | gctctacttc | gtctctggag | tttcgtctct ggagtttcag | 420 |
| gtccgagcgg | ctaactcggt | cctaggcgtc | tcccgtgccg | cgccccgaa gggacagtct | 480 |
| tgctggactg | gtctcacggt | agcgcatacc | cgaatcagat | tcgtggtgac gcgcaaaacc | 540 |
| gtgatctcac | atttacagat | tcccgtgcat | ccgtgtgcac | ggattcacgc ccatctgggc | 600 |
| attcacgtgg | ccgttttggt | gcctccgtct | gggctctcgt | cgctcccggc ggcgcgtcgt | 660 |
| ggtgacaacc | gcgttcgacg | cggcagagat | tgccgccgcg | gtcccggaat ctggctcacc | 720 |
| gtgcagcggt | acagcgtcag | ctcgactgcg | cagaatccgc | gccaaggaag cccgcagggc | 780 |
| gtcgatcgaa | cgctgtgggg | cggtgccggc | cgcggtgccg | atgtggtcgt cgcgggagtt | 840 |
| gtggactgcc | gatctgcggg | tgcttttgtc | gggtccggag | ttcagcacgc gccgggtgat | 900 |
| ttcggcggcg | acggtgctcg | ctgtcgcggt | ggcgatggcc | gagttcgccg accatgccac | 960 |
| gggccgcaat | gtggcggtga | caaacgaggt | tctggccgag | cgcgcgaggt gttctaagcg | 1020 |
| ttcggtgacc | gcgcgcgcg | gggtgttgaa | agcgttgggt | gtcgcggtgg aagcggtacg | 1080 |
| tgggcatggc | tctgcgacca | cacacacggt | cggtaatcga | ccgagcattt ggcacctggt | 1140 |
| aagccgacgc | cagcccacca | tcgacaaccc | gcccacggcc | ccgcagaacg gccgcggcga | 1200 |
| gcctgccgat | acggtgcccg | atcgcggcca | gagcgcgccc | gtggctgtgg agacttgcga | 1260 |
| cctaccacca | tcccgtaggg | ataggtgggt | aactcctgtt | gagaattact caccaagcac | 1320 |
| gcgcgagcgc | gcgagcgcgg | aaaattcttc | cccaaaacaa | acacaaccgg cgcggtcgcg | 1380 |
| gcggcgctac | cgcgccacgc | cgcgcccct | ggacgttcag | cgactcgccg ccggcctggt | 1440 |
| cacgccggca | gtcggccacg | gcccagacaa | cgacgggcgg | cgaaccgcgc tgatcgccgg | 1500 |
| cctggagcag | ggccatatcg | gggccatctg | cgacgcgatc | acgacggccg gcatcgacgc | 1560 |
| gaccgcctgg | actccgaaga | cgctcacggc | ggcactgaac | gccgacgcgc gggtgaccgg | 1620 |
| ctggtcgtgg | ccggatcgca | tcgaacgtcc | tggcgcgttc | ctggcgtcgc ggctgcgccg | 1680 |
| cctgcccgca | cggcccgaca | ccagtggccc | ggttgacaac | ggcctggatc aggcccgtag | 1740 |
| gacacccgtt | gagccgtcag | cggcccgtgt | agcgccggta | cagacggccg ctggccgcgc | 1800 |
| gtacgcccgt | gcgttgttcg | ccgagcagcg | acggcaccgg | gtgaccgccg ccaatgccca | 1860 |
| gtcagccgcg | gtgccggtgc | gccaaagtgc | gccagaaacc | gcggtgtgcg caacgtgcgg | 1920 |
| atgctcggac | gcaccacggc | ggcggttcct | gccaacgcgg | cgggctcaca tttgcgatgc | 1980 |
| ctgtttccaa | ggatgtggtg | gtgggcaggc | gcgtactggt | cgcgtcggaa cggtcggcag | 2040 |
| cagttccgcg | gtgccacagt | gccagtagtc | gggcagggct | tgcacgggga tgcggaccca | 2100 |

```
tccgccggcc gcggccggcg atgggtccag tgtcgcgtta gggccgtcgt ccagccgcgc    2160
cagctcgcgg tcgatgcgca tcagcttggc accgtagatg tcgtcgtggc ggcggtccca    2220
cgtgttggtg atgcggtcgc ggtaccagcc tgtccagtct tcgccggtgc cgccggcggt    2280
gagcccggcc cggtaccacg cttcgaggcg atcacggccc cgtgcgtggt tgatggtctg    2340
ggccgcagcc cagtccgcgt cacggagggc tctgtcggct tcgtccatga acccgcgccg    2400
ggtcatgtcg atgatggctg cgacggggc gtcgtagggg cctggcatgg gcggaggcag    2460
tcggaactgt tgcggtttgc ttgcgttcag ttcctcgtcc tgctggtggg tgcggtcgtg    2520
cagggcaagg ctgtcgcggt accaggcgtc gagcgcggtg cgccagtccc cgccagtggc    2580
gtagggctcc cacggttgcg gtggcagggt ggtgaactcg tgcaggacca ggccgtcgat    2640
gtcgtcgcgc agttcttcac cggcgatggc ggcgatgcgg gcgcagtagc cgggcagatg    2700
gctacgccag tcggcgggca gttcgccgct gcgcgcccac cgcagcacat cggcccacaa    2760
cccaagggcg aattctgcag atatcggtga ccacaacgac gcgcccgctt tgatcgggga    2820
cgtctgcggc cgaccattta cgggtcttgt tgtcgttggc ggtcatgggc cgaacatact    2880
cacccggatc ggagggccga ggacaaggtc gaacgagggg catgacccgg tgcggggctt    2940
cttgcactcg gcataggcga gtgctaagaa taacgttggc actcgcgacc ggtgagtcgt    3000
aggtcgggac ggtgaggcca ggcccgtcgt cgcagcgagt ggcagcgagg acaacttgag    3060
ccgtccgtcg cgggcactgc gcccggccag cgtaagtagc ggggttgccg tcacccggtg    3120 accccggtt tcatccccga tccggaggaa tcacttcgca atgcctatag tgcagaacct    3180
ccaggggcaa atggtacatc aggccatatc acctagaact ttaaatgcat gggtaaaagt    3240
agtagaagag aaggctttca gcccagaagt aatacccatg ttttcagcat tatcagaagg    3300
agccacccca caagatttaa ataccatgct aaacacagtg gggggacatc aagcagccat    3360
gcaaatgtta aaagagacca tcaatgagga agctgcagaa tgggatagat tgcatccagt    3420
gcatgcaggg cctattgcac caggccagat gagagaacca aggggaagtg acatagcagg    3480
aactactagt acccttcagg aacaaatagg atggatgaca cataatccac ctatcccagt    3540
aggagaaatc tataaaagat ggataatcct gggattaaat aaaatagtaa gaatgtatag    3600
ccctaccagc attctggaca taagacaagg accaaaggaa ccctttagag actatgtaga    3660
ccgattctat aaaactctaa gagccgagca agcttcacaa gaggtaaaaa attggatgac    3720
agaaaccttg ttggtccaaa atgcgaaccc agattgtaag actattttaa aagcattggg    3780
accaggagcg acactagaag aaatgatgac agcatgtcag ggagtggggg gacctggcca    3840
taaggcaaga gttttgtagt ctagagggcc caattcgccc tatagtgagt cgtattacaa    3900
ttcactggcc gtcgttttac aacgtcgtga ctgggaaaac cctggcgtta cccaacttaa    3960
tcgccttgca gcacatcccc ctttcgccag ctggcgtaat agcgaagagg cccgcaccga    4020
tcgcccttcc caacagttgc gcagcctgaa tggcgaatgg acgcgccctg tagcggcgca    4080
ttaagcgcgg cgggtgtggt ggttacgcgc agcgtgaccg ctacacttgc cagcgcccta    4140
gcgcccgctc ctttcgcttt cttcccttcc tttctcgcca cgttcgccgg ctttccccgt    4200
caagctctaa atcgggggct ccctttaggg ttccgattta gtgctttacg gcacctcgac    4260
cccaaaaaac ttgattaggg tgatggttca cgtagtgggc catcgccctg atagacggtt    4320
tttcgccctt tgacgttgga gtccacgttc tttaatagtg gactcttgtt ccaaactgga    4380
acaacactca accctatctc ggtctattct tttgatttat aagggatttt gccgatttcg    4440
gcctattggt taaaaaatga gctgatttaa caaaaattta acgcgaattt taacaaaatt    4500
```

```
cagggcgcaa gggctgctaa aggaagcgga acacgtagaa agccagtccg cagaaacggt    4560
gctgaccccg gatgaatgtc agctactggg ctatctggac aagggaaaac gcaagcgcaa    4620
agagaaagca ggtagcttgc agtgggctta catggcgata gctagactgg gcggttttat    4680
ggacagcaag cgaaccggaa ttgccagctg gggcgccctc tggtaaggtt gggaagccct    4740
gcaaagtaaa ctggatggct ttcttgccgc caaggatctg atggcgcagg ggatcaagat    4800
ctgatcaaga gacaggatga ggatcgtttc gcatgattga acaagatgga ttgcacgcag    4860
gttctccggc cgcttgggtg gagaggctat tcggctatga ctgggcacaa cagacaatcg    4920
gctgctctga tgccgccgtg ttccggctgt cagcgcaggg gcgcccggtt cttttttgtca   4980 agaccgacct gtccggtgcc ctgaatgaac tgcaggacga ggcagcgcgg ctatcgtggc    5040
tggccacgac gggcgttcct tgcgcagctg tgctcgacgt tgtcactgaa gcgggaaggg    5100
actggctgct attgggcgaa gtgccggggc aggatctcct gtcatcccac cttgctcctg    5160
ccgagaaagt atccatcatg gctgatgcaa tgcggcggct gcatacgctt gatccggcta    5220
cctgcccatt cgaccaccaa gcgaaacatc gcatcgagcg agcacgtact cggatggaag    5280
ccggtcttgt cgatcaggat gatctggacg aagagcatca ggggctcgcg ccagccgaac    5340
tgttcgccag gctcaaggcg cgcatgcccg acggcgagga tctcgtcgtg acccatggcg    5400
atgcctgctt gccgaatatc atggtggaaa atggccgctt ttctggattc atcgactgtg    5460
gccggctggg tgtggcggac cgctatcagg acatagcgtt ggctacccgt gatattgctg    5520
aagagcttgg cggcgaatgg gctgaccgct tcctcgtgct ttacggtatc gccgctcccg    5580
attcgcagcg catcgccttc tatcgccttc ttgacgagtt cttctgaatt gaaaaaggaa    5640
gagtatgagt attcaacatt tccgtgtcgc ccttattccc ttttttgcgg cattttgcct    5700
tcctgttttt gctcacccag aaacgctggt gaaagtaaaa gatgctgaag atcagttggg    5760
tgcacgagtg ggttacatcg aactggatct caacagcggt aagatccttg agagttttcg    5820
ccccgaagaa cgttttccaa tgatgagcac ttttaaagtt ctgctatgtg gcgcggtatt    5880
atcccgtatt gacgccgggc aagagcaact cggtcgccgc atacactatt ctcagaatga    5940
cttggttgag tactcaccag tcacagaaaa gcatcttacg gatggcatga cagtaagaga    6000
attatgcagt gctgccataa ccatgagtga taacactgcg gccaacttac ttctgacaac    6060
gatcggagga ccgaaggagc taaccgcttt tttgcacaac atgggggatc atgtaactcg    6120
ccttgatcgt tgggaaccgg agctgaatga agccatacca aacgacgagc gtgacaccac    6180
gatgcctgta gcaatggcaa caacgttgcg caaactatta actggcgaac tacttactct    6240
agcttcccgg caacaattaa tagactggat ggaggcggat aaagttgcag gaccacttct    6300
gcgctcggcc cttccggctg gctggtttat tgctgataaa tctggagccg gtgagcgtgg    6360
gtctcgcggt atcattgcag cactggggcc agatggtaag ccctcccgta tcgtagttat    6420
ctacacgacg gggagtcagg caactatgga tgaacgaaat agacagatcg ctgagatagg    6480
tgcctcactg attaagcatt ggtaactgtc agaccaagtt tactcatata ctttagat     6540 tgatttaaaa cttcattttt aatttaaaag gatctaggtg aagatccttt ttgataatct    6600
catgaccaaa atcccttaac gtgagttttc gttccactga gcgtcagacc ccgtagaaaa    6660
gatcaaagga tcttcttgag atcctttttt tctgcgcgta atctgctgct tgcaaacaaa    6720
aaaaccaccg ctaccagcgg tggtttgttt gccggatcaa gagctaccaa ctcttttcc    6780 gaaggtaact ggcttcagca gagcgcagat accaaatact gttcttctag tgtagccgta    6840
```

```
                                                           -continued
gttaggccac cacttcaaga actctgtagc accgcctaca tacctcgctc tgctaatcct    6900
gttaccagtg gctgctgcca gtggcgataa gtcgtgtctt accgggttgg actcaagacg    6960
atagttaccg gataaggcgc agcggtcggg ctgaacgggg ggttcgtgca cacagcccag    7020
cttggagcga acgacctaca ccgaactgag atacctacag cgtgagctat gagaaagcgc    7080
cacgcttccc gaagggagaa aggcggacag gtatccggta agcggcaggg tcggaacagg    7140
agagcgcacg agggagcttc caggggggaaa cgcctggtat ctttatagtc ctgtcgggtt    7200
tcgccacctc tgacttgagc gtcgattttt gtgatgctcg tcagggggggc ggagcctatg    7260 gaaaaacgcc agcaacgcgg cctttttacg gttcctggcc ttttgctggc cttttgctca    7320
catgttcttt cctgcgttat ccctgattc tgtggataac cgtattaccg cctttgagtg    7380
agctgatacc gctcgccgca gccgaacgac cgagcgcagc gagtcagtga gcgaggaagc    7440
ggaag                                                                7445
```